(12) United States Patent
Garbero et al.

(10) Patent No.: US 9,234,224 B2
(45) Date of Patent: Jan. 12, 2016

(54) BIOMASS PRETREATMENT PROCESS

(75) Inventors: Mirko Garbero, Turin (IT); Piero Ottonello, Genoa (IT); Marco Cotti Comettini, Trivero (IT); Simone Ferrero, Tortona (IT); Paolo Torre, Arenzano (IT); Francesco Cherchi, Campobasso (IT); Andrea Bonanni, Rome (IT)

(73) Assignee: Beta Renewables, S.p.A., Tortona (AL) (IT)

( * ) Notice: Subject to any disclaimer, the term of this patent is extended or adjusted under 35 U.S.C. 154(b) by 1039 days.

(21) Appl. No.: 13/260,340

(22) PCT Filed: Mar. 31, 2010

(86) PCT No.: PCT/IB2010/051412
§ 371 (c)(1),
(2), (4) Date: Sep. 25, 2011

(87) PCT Pub. No.: WO2010/113129
PCT Pub. Date: Oct. 7, 2010

(65) Prior Publication Data
US 2012/0104313 A1 May 3, 2012

(30) Foreign Application Priority Data

Mar. 31, 2009 (WO) .................. PCT/IT2009/000125
Mar. 31, 2009 (WO) .................. PCT/IT2009/000129
Mar. 31, 2009 (WO) .................. PCT/IT2009/000130

(51) Int. Cl.
*C08H 8/00* (2010.01)
*C12P 19/02* (2006.01)
(Continued)

(52) U.S. Cl.
CPC . *C12P 19/02* (2013.01); *C08H 8/00* (2013.01);
*C12P 19/04* (2013.01); *C13K 1/02* (2013.01);
*D21C 5/005* (2013.01); *C12P 2201/00* (2013.01); *Y02E 50/16* (2013.01)

(58) Field of Classification Search
None
See application file for complete search history.

(56) References Cited

U.S. PATENT DOCUMENTS 3,212,932 A    10/1965   Hess et al.
4,342,831 A    8/1982   Faber et al.
(Continued)

FOREIGN PATENT DOCUMENTS

WO    2006024242 A    3/2006
WO    2006034590 A    4/2006
(Continued)

OTHER PUBLICATIONS

Capparos, Sebastian et al, Xylooligosaccharides production from Arundo donax, Journal of Agricultural and Food Chemistry, Jul. 2007, 5536-5543, vol. 55, No. 14.
(Continued)

*Primary Examiner* — Necholus Ogden, Jr.
(74) *Attorney, Agent, or Firm* — Edwin A. Sisson, Attorney at Law, LLC; Jeffrey J. Banyas

(57) ABSTRACT

The process for the treatment of ligno-cellulosic biomass comprises the steps of:
A) Soaking a ligno-cellulosic biomass feedstock in vapor or liquid water or mixture thereof in the temperature range of 100 to 210° C. for 1 minute to 24 hours to create a soaked biomass containing a dry content and a first liquid;
B) Separating at least a portion of the first liquid from the soaked biomass to create a first liquid stream and a first solid stream; wherein the first solid stream comprises the soaked biomass; and
C) Steam exploding the first solid stream to create a steam exploded stream comprising solids and a second liquid.

13 Claims, 9 Drawing Sheets

(51) Int. Cl.
*C12P 19/04* (2006.01)
*C13K 1/02* (2006.01)
*D21C 5/00* (2006.01)

(56) References Cited

U.S. PATENT DOCUMENTS 5,366,558 A 11/1994 Brink
8,778,084 B2 * 7/2014 Nguyen et al. .................. 127/1
2010/0041119 A1 * 2/2010 Christensen et al. ......... 435/162

FOREIGN PATENT DOCUMENTS

WO 2007009463 A 1/2007
WO 2008095098 A2 8/2008

OTHER PUBLICATIONS

McMillan, J.D., Process for Pretreating Lignocellulosic Biomass: A Review, Database NTIS (Online) National Technical Information Service, 1992, NREL Report No. TP-421-4978, US Department of Commerce, Springfield, VA.

Huang, H.J. et al, A review of separation technologies in current and future biorefineries, Separation and Purification Technology, Aug. 1, 2008, 1-21, vol. 62, No. 1, Elsevier Science, Amsterdam, NL.

Wang, M., Manufacture of fuel ethanol involves hydrolyzing solid fermented sweet sorghum stalk using enzyme, forming pentose and glucose liquid followed by fermenting pentose and glucose liquid together, WPI, Mar. 12, 2008, vol. 2009, No. 4, Thomson.

Nandini, C.D. et al, Carbohydrate composition of wheat, wheat bran, sorghum and bajra with good chapati/roti (Indian flat bread) making quality, Food Chemistry, May 1, 2001, 197-203, vol. 73, No. 2, Elsevier Ltd.

Sepulveda-Huerta, E et al, Production of detoxified sorghum straw hydrolysates for fermentative purposes, Journal of the Science of Food and Agriculture, Dec. 1, 2006, 2579-2586, vol. 86, No. 15, Wiley & Sons, Chichester, GB.

International Search Report.

* cited by examiner

BIOMASS PRETREATMENT PROCESS

PRIORITY AND CROSS REFERENCES

This patent application claims the priority from PCT/IT2009/000125 (IT) filed 31 Mar. 2009; PCT/IT2009/000129 (IT) filed 31 Mar. 2009; and PCT/IT2009/000130 (IT) filed 31 Mar. 2009.

BACKGROUND

In the biomass field converting lignocellulosic biomass to ethanol is a common practice. If the biomass is a polysaccharide-containing biomass and it is lignocellulosic, a pre-treatment is often used to ensure that the structure of the lignocellulosic content is rendered more accessible to the enzymes, and at the same time the concentrations of harmful inhibitory by-products such as acetic acid, furfural and hydroxymethyl furfural are usually high and present problems in further processing.

In general terms the more severe the treatment, the more accessible are the cellulosic contents of the material. The severity of the steam explosion is known in the literature as Ro, and is a function of time and temperature expressed as $$Ro = t \cdot e^{[(T-100)/14.75]}$$

with temperature, T, expressed in Celsius and time, t, expressed in common units. The formula is also expressed as Log(Ro), namely $$\mathrm{Log}(Ro) = \mathrm{Ln}(t) + [(T-100)/14.75].$$

It is generally considered that a high Ro value is associated with a high number of unwanted by-products which inhibit the hydrolysis and fermentation of the biomass, such as furfural.

NREL Report No. TP-421-4978, November 1992, McMillan J. D., "Processes for Pretreating Lignocellulosic Biomass: A Review" even affirmed in its conclusions that "steam explosion-based processes . . . are unattractive in the long run because the formation of degradation products reduces yields" and exhorted to research alternative processes, such as ammonia fiber explosion and supercritical fluid-based treatments.

There exists therefore, the need to have a severe process with a high Ro which at the same time produces a product with low furfural.

SUMMARY

Disclosed in this specification is a process for the improved pretreatment of biomass which includes the steps of soaking a biomass feedstock in vapor or liquid water in the temperature range of 100 to 210° C., preferably 140 to 210° C., for 1 minute to 24 hours, preferably 1 minute to 16 hours, more preferably 1 minute to 2.5 hours, and most preferably 1 minute to 2 hours to create a soaked biomass containing a dry content and a first liquid; separating at least a portion of the first liquid from the soaked biomass to create a first liquid stream and a first solid stream, wherein the first solid stream comprises the soaked biomass; steam exploding the first solid stream to create a steam exploded stream comprising solids and a second liquid; optionally separating at least some of the second liquid from the steam exploded stream to create a second liquid stream and a second solid stream. It is also disclosed that the process may comprises the further step of combining at least a portion of the liquid of the first liquid stream with the second solid stream.

A third optional step is also disclosed in which the steam exploded stream is washed with at least a third liquid to create a third liquid stream prior to introduction of the steam exploded stream into the separation step.

A further purification step is disclosed wherein the first liquid stream is purified to create a first purified liquid stream prior to combining the first liquid stream with the second solid stream.

A further step is disclosed wherein the second liquid stream is purified to create a second purified liquid stream and then the second purified liquid stream is combined with the second solid stream.

It is further disclosed to purify the third liquid stream and then combine it with the second solid stream.

Pressing is disclosed as a way to separate the liquid from the soaked biomass.

Flashing is disclosed as a step to purify the first liquid stream. It is further disclosed that this flashing be done without reducing the pressure of the first liquid stream to atmospheric pressure before flashing. It is further disclosed that the flashing be done at the pressure of the first liquid stream at the end of separating the first liquid from the soaked biomass.

Steam stripping of any and all of the liquid streams in combination or separately is disclosed. Using the steam from steam explosion step and/or the soaking step is also disclosed.

Purification of any of the liquid streams with activated charcoal is also disclosed. It is also disclosed to concentrate the streams to remove water. It is also disclosed that the streams can be combined after at least a portion of the second solid stream has been hydrolyzed.

Also disclosed in this specification is a novel composition from the process comprising a solid, a liquid, an amount of C5's based upon the amount of arabinan and xylan and the monomers, dimers, oligomers and polymers of arabinose and xylose in the liquid and solid of the composition, an amount of C6's based upon the glucan content which includes the monomers, dimers, oligomers and polymers of glucan in the liquid and solid of the composition and furfural wherein the ratio of the amount of C5's to the amount of C6's is less than 0.50 and the ratio of amount of the furfural, which is always present in the composition to the amount of C5's and C6's added to together is between 0 and 0.0140, also expressed as greater than 0 and less than 0.0140; is between 0 and 0.0100, also expressed as greater than 0 and less than 0.0100; is between 0 and 0.0060, also expressed as greater than 0 and less than 0.0060; is between 0 and 0.0040, also expressed as greater than 0 and less than 0.0040; 0 and 0.0030, also expressed as greater than 0 and less than 0.0030; 0 and 0.0020, also expressed as greater than 0 and less than 0.0020; 0 and 0.0010, also expressed as greater than 0 and less than 0.0010; or between 0 and 0.0009, also expressed as greater than 0 and less than 0.0009. It is further disclosed that the ratio of the amount of C5's to the amount of C6's is less than 0.44.

Another novel composition of biomass is disclosed comprising a solid, a liquid, an amount of C5's based upon the amount of arabinan and xylan and the monomers, dimers, oligomers and polymers of arabinose and xylose in the liquid and solid of the composition, an amount of C6's based upon the glucan content which includes the monomers, dimers, oligomers and polymers of glucan in the liquid and solid of the composition and furfural wherein the ratio of the amount of C5's to the amount of C6's is greater than 0.50 and the ratio of amount of the furfural to the amount of C5's and C6's added to together is any of the ranges of between 0 and 0.09, also expressed as greater than 0 and less than 0.09; between 0 and 0.0060, also expressed as greater than 0 and less than 0.0060; between 0 and 0.0050, also expressed as greater than 0 and less than 0.0050; between 0 and 0.0040; between 0 and 0.0030, also expressed as greater than 0 and less than 0.0030 and between 0 and 0.0016, also expressed as greater than 0 and less than 0.0016.

It is further disclosed that the amount of solids by total weight of either of the novel compositions be in any of the ranges of 3 to 85%, 3 to 65%, 3 to 20% 11 to 99%; 14 to 99%; 16 to 99%; 19 to 99%; 21 to 99%; 24 to 99%; 26 to 99%; 29 to 99%; 31 to 99%; 36 to 99%; and 41 to 99%.

DETAILED DESCRIPTION

Figure 1:
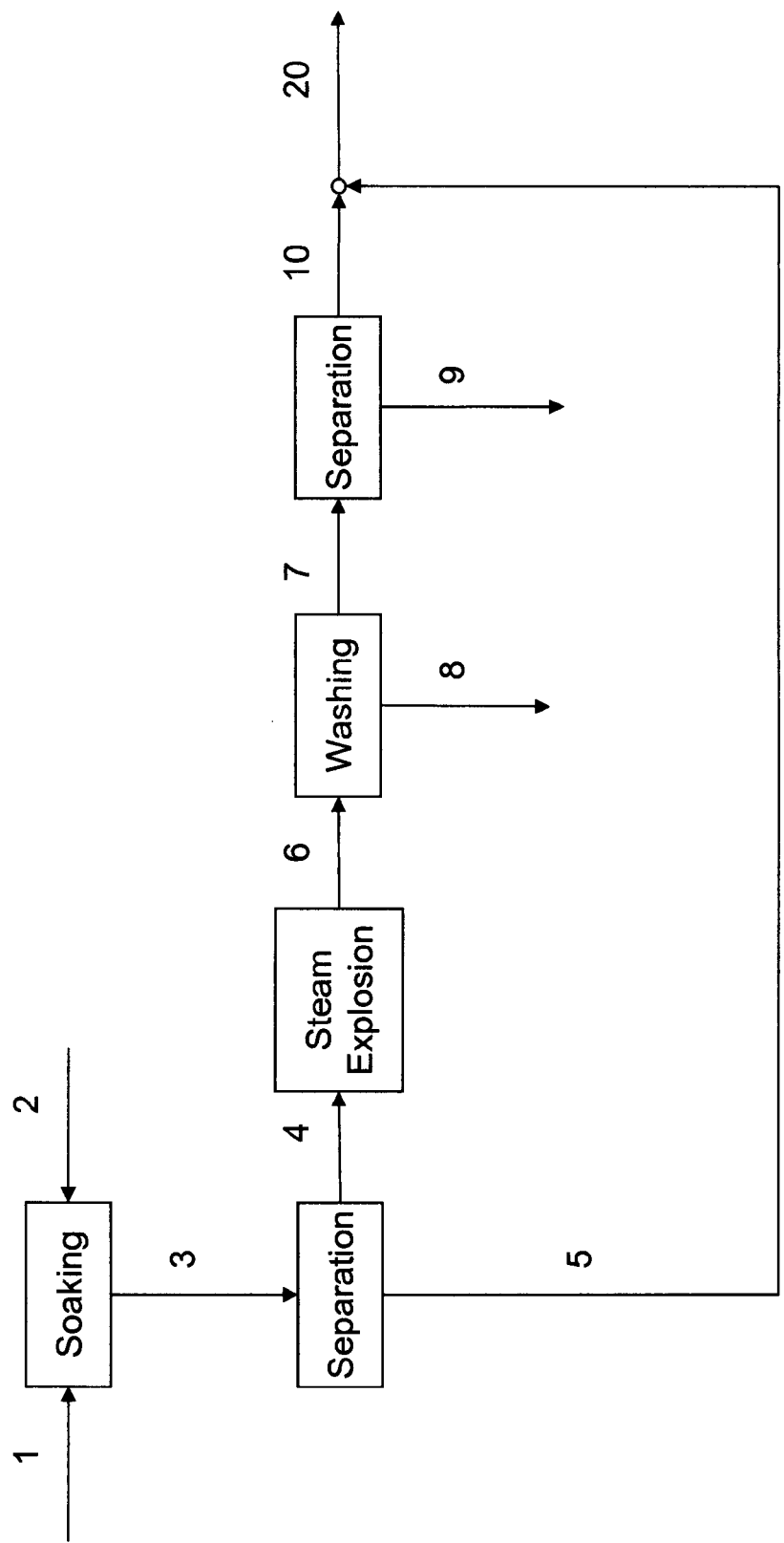
FIG. 1 is a schematic of an embodiment of the process.

In all instances of this text, the word "stream" is used to mean that it is comprised of the material as well. For instance, the second liquid stream would be comprised of the second liquid, the second purified liquid stream is comprised of the second purified liquid. Combining streams means the materials in the streams are mixed.

The process acts upon a feedstock in a feedstock stream. The feedstock stream is comprised of biomass having a dry content and water. Usually the water is not free water, but is water absorbed into the biomass itself. This biomass is often expressed according to its dry content (non-water). A 20% dry content biomass corresponds to a biomass that has 80% water and 20% non-water, or otherwise solid content. The term biomass and water is the dry content of the biomass plus the absorbed and free water and water which may have been added. For example, the amount of biomass plus water for 100 kg of biomass with 20% dry content is 100 kg. The amount of biomass plus water for 100 kg of biomass with 20% dry content plus 10 kg of water is 110 kg.

The process described is believed capable of utilizing a feedstock stream of biomass and water where the dry matter content to water of the feedstock stream is preferably 20-80%, or 21-80%, preferably 25-70%, or 26-70%, more preferably 25-60%, or 26-60%, even more preferably 25-50%, or 26-50% or 25-40%, or 26% to 40% and most preferably 25-35%, or 26-35%, or 26-34%, or 31%-49%.

After treatment, the amount of solids by total weight of the compositions can be in any of the ranges of 3 to 85%, 3 to 85%, 3 to 65%, 3 to 20%, 11 to 99%; 14 to 99%; 16 to 99%; 19 to 99%; 21 to 99%; 24 to 99%; 26 to 99%; 29 to 99%; 31 to 99%; 36 to 99%; and 41 to 99%.

This can alternatively be expressed as a minimum dry content, i.e. as a weight percent of the dry content relative to the water in the feedstock stream. This would correspond to at least 20 weight percent dry content, preferably at least 25 weight percent dry content, more preferably at least 30 weight percent dry content, and most preferably at least 40 weight percent dry content. The upper limit of these contents is by definition 100%, but in practice 80 weight percent would be the upper limit to these contents if they were expressed in ranges.

Therefore, ranges suitable for this invention are biomasses having dry contents of greater than 3%, 15%, 20%, 21%, 25%, 26%, 30%, 31%, 35%, 36%, 40%, 50%, 60% and 80% with an upper limit of 100% or 90% for each lower limit.

The distribution of fiber and particle sizes of the biomass may involve the ranges of 0-150 mm, preferably, 5-125 mm, more preferably, 10-100 mm, even more preferably 15-30 to 90 mm or 20-80 mm and most preferably 26 to 70 mm.

The preferred distribution of fiber and particle sizes is defined as at least 20% (w/w) of the biomass ranging within the preferred interval.

Plant biomass is a preferred feedstock. Apart from starch the three major constituents in plant biomass are cellulose, hemicellulose and lignin, which are commonly referred to by the generic term lignocellulose. Polysaccharide-containing biomasses as a generic term include both starch and lignocellulosic biomasses. Therefore, some types of feedstocks can be plant biomass, polysaccharide containing biomass, and lignocellulosic biomass. A typical lignocellulosic biomass will contain cellulose, with amounts being at least 5 percent by weight of the total amount of dry biomass, with at least 10% and 20% by weight of the total amount of dry biomass. The ligno-cellulosic biomass may also contain starch in the amounts preferably less than 50% by weight, with less than 45, 35 and 15 weight percents even more preferred.

If the biomass is a polysaccharide-containing biomass and it is lignocellulosic, a pre-treatment is often used to ensure that the structure of the lignocellulosic content is rendered more accessible to the enzymes, and at the same time the concentrations of harmful inhibitory by-products such as acetic acid, furfural and hydroxymethyl furfural remain substantially low.

Polysaccharide-containing lignocellulosic biomasses according to the present invention include any material containing polymeric sugars e.g. in the form of starch as well as refined starch, cellulose and hemicellulose.

Relevant types of cellulosic biomasses and polysaccharide ligno-cellusosic biomasses for hydrolysis and pretreatment according to the present invention may include biomasses derived from grasses and more specifically agricultural crops such as e.g.: starch e.g. starch containing grains and refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like with a similar dry matter content.

The ligno-cellulosic biomass feedstock is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass Leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals. This complex structure can be seen in the image on the left, portraying a wheat (*Triticum aestivum*) spike.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchardgrass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indiangrass, bermudagrass and switchgrass.

One classification of the grass family recognizes twelve subfamilies: These are 1) anomochlooideae, a small lineage of broad-leaved grasses that includes two genera (*Anomochloa, Streptochaeta*); 2) Pharoideae, a small lineage of grasses that includes three genera, including *Pharus* and *Leptaspis;* 3) Puelioideae a small lineage that includes the African genus *Puelia*; 4) Pooideae which includes wheat, barely, oats, brome-grass (Bronnus) and reed-grasses (*Calamagrostis*); 5) Bambusoideae which includes bamboo; 6) Ehrhartoideae, which includes rice, and wild rice; 7) Arundinoideae, which inludes the giant reed and common reed 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and bluestem grasses. 11) Micrairoideae; 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Therefore a preferred lignocellulosic biomass is selected from the group consisting of the grasses. Alternatively phrased, the preferred lignocellulosic biomass is selected from the group consisting of the plants belonging to the Poaceae or Gramineae family.

If the polysaccharide-containing biomasses are lignocellulosic, the material may be cut into pieces where 20% (w/w) of the biomass preferably ranges within 26-70 mm, before pre-treatment. The pre-treated material has preferably a dry matter content above 20% before entering the process. Besides liberating the carbohydrates from the biomass, the pre-treatment process sterilizes and partly dissolves the biomass and at the same time washes out potassium chloride from the lignin fraction.

The biomass will contain some compounds which are hydrolysable into a water-soluble species obtainable from the hydrolysis of the biomass. For example, cellulose can be hydrolyzed into glucose, cellobiose, and higher glucose polymers and includes dimers and oligomers. Cellulose is hydrolyzed into glucose by the carbohydrolytic cellulases. The prevalent understanding of the cellulolytic system divides the cellulases into three classes; exo-1,4-β-D-glucanases or cellobiohydrolases (CBH) (EC 3.2.1.91), which cleave off cellobiose units from the ends of cellulose chains; endo-1,4-β-D-glucanases (EG) (EC 3.2.1.4), which hydrolyse internal β-1,4-glucosidic bonds randomly in the cellulose chain; 1,4-β-D-glucosidase (EC 3.2.1.21), which hydrolyses cellobiose to glucose and also cleaves off glucose units from cellooligosaccharides. Therefore, if the biomass contains cellulose, then glucose is a water soluble hydrolyzed species obtainable from the hydrolysis of the biomass.

By similar analysis, the hydrolysis products of hemicellulose are water soluble species obtainable from the hydrolysis of the biomass, assuming of course, that the biomass contains hemicellulose. Hemicellulose includes xylan, glucuronoxylan, arabinoxylan, glucomannan, and xyloglucan. The different sugars in hemicellulose are liberated by the hemicellulases. The hemicellulytic system is more complex than the cellulolytic system due to the heterologous nature of hemicellulose. The systems may involve among others, endo-1,4-β-D-xylanases (EC 3.2.1.8), which hydrolyse internal bonds in the xylan chain; 1,4-β-D-xylosidases (EC 3.2.1.37), which attack xylooligosaccharides from the non-reducing end and liberate xylose; endo-1,4-β-D-mannanases (EC 3.2.1.78), which cleave internal bonds; 1,4-β-D-mannosidases (EC 3.2.1.25), which cleave mannooligosaccharides to mannose. The side groups are removed by a number of enzymes; such as α-D-galactosidases (EC 3.2.1.22), α-L-arabinofuranosidases (EC 3.2.1.55), α-D-glucuronidases (EC 3.2.1.139), cinnamoyl esterases (EC 3.1.1.-), acetyl xylan esterases (EC 3.1.1.6) and feruloyl esterases (EC 3.1.1.73).

Referring to FIG. 1, the first step in the process is the soaking of a biomass feedstock stream 1 in a substance such as water in either vapor form, steam, or liquid form or liquid and steam together, labeled stream 2, to produce a product 3. The product 3 is a soaked biomass containing a first liquid, with the first liquid usually being water in its liquid or vapor form or some mixture.

This soaking can be done by any number of techniques that expose a substance to water, which could be steam or liquid or mixture of steam and water, or, more in general, to water at high temperature and high pressure. The temperature should be in one of the following ranges: 145 to 165° C., 120 to 210° C., 140 to 210° C., 150 to 200° C., 155 to 185° C., 160 to 180° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

Figure 9:
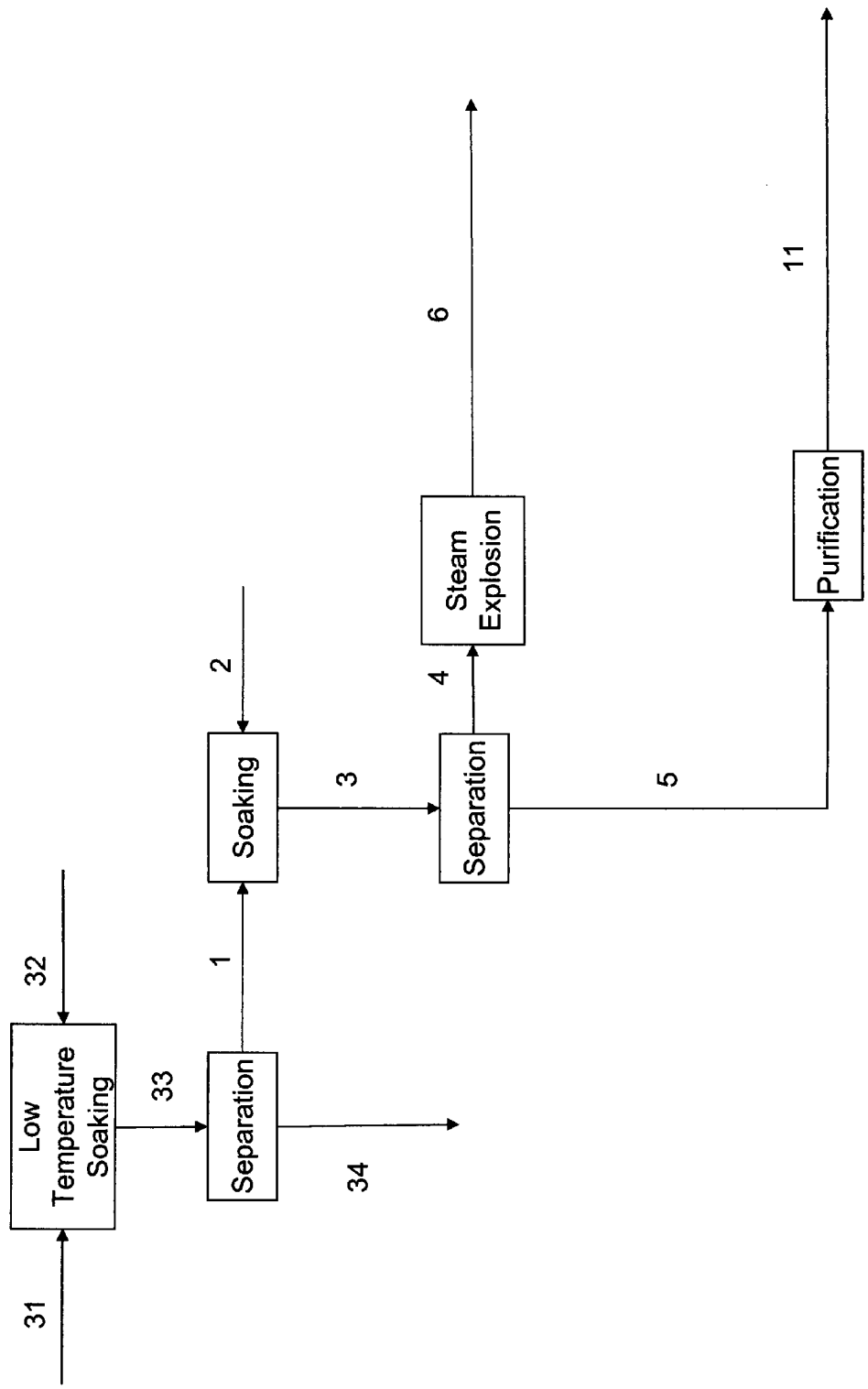
FIG. 9 is a schematic of a ninth embodiment of the process.

If steam is used, it is preferably saturated, but could be superheated. The soaking step can be batch or continuous, with or without stirring. Another embodiment is shown in FIG. 9, which has a low temperature soak prior to the high temperature soak. The temperature of the low temperature soak is in the range of 25 to 90° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

This low temperature soak is shown in FIG. 9 with 31 being the biomass feedstock, 32 is the water or liquid, 33 is the low temperature soaked biomass. 34 is the liquid, and would be a fourth liquid stream that has been separated from the low temperature soaked biomass with 1 being the biomass feedstock after low temperature soaking.

Either soaking step could also include the addition of other compounds, e.g. $H_2SO_4$, $NH_3$, in order to achieve higher performance later on in the process.

The product 3 comprising the first liquid is then passed to a separation step where the first liquid is separated from the soaked biomass. The liquid will not completely separate so that at least a portion of the liquid is separated, with preferably as much liquid as possible in an economic time frame. The liquid from this separation step is known as the first liquid stream comprising the first liquid, labeled 5 in FIG. 1. The first liquid will be the liquid used in the soaking, generally water and the soluble species of the feedstock. As shown in the Tables 1 through 16, these water soluble species are glucan, xylan, galactan, arabinan, glucolygomers, xyloolygomers, galactolygomers and arabinolygomers. The solid biomass, labeled 4, is called the first solid stream as it contains most, if not all, of the solids.

The separation of the liquid can again be done by known techniques and likely some which have yet been invented. A preferred piece of equipment is a press, as a press will generate a liquid under high pressure which is useful as described later.

The first solid stream 4 is then steam exploded to create a steam exploded stream 6. Steam explosion is a well known technique in the biomass field and any of the systems available today and in the future are believed suitable for this step. The severity of the steam explosion is known in the literature as Ro, and is a function of time and temperature and is expressed as $$Ro = te^{[(T-100)/14.75]}$$

with temperature, T expressed in Celsius and time, t, expressed in common units.

The formula is also expressed as Log(Ro), namely $$Log(Ro) = Ln(t) + [(T-100)/14.75].$$

As disclosed in the operating conditions below, this process will produce a solids composition under a high Ro, and that is novel in its low furfural content. As shown in the data, furfural is not a naturally occurring compound in biomass. Furfural is made when the biomass is exposed to high temperatures.

Log(Ro) is preferably in the ranges of 2.8 to 5.3, 3 to 5.3, 3 to 5.0 and 3 to 4.3.

The steam exploded stream may be optionally washed at least with water and there may be other additives used as well. It is conceivable that another liquid may used in the future, so water is not believed to be absolutely essential. At this point, water is the preferred liquid and if water is used, it is considered the third liquid. The liquid effluent from the optional wash is the third liquid stream 8. Although shown in the drawing accompanying this specification, this wash step is not considered essential and is optional.

The washed steam exploded stream comprising the washed exploded biomass is labeled 7. The washed exploded stream is then processed to remove at least a portion of the liquid in the washed exploded material. This separation step is also optional. The term at least a portion is removed, is to remind one that while removal of as much liquid as possible is desirable (pressing), it is unlikely that 100% removal is possible. In any event, 100% removal of the water is not desirable since water is needed for the subsequent hydrolysis reaction. The preferred process for this step is again a press, but other known techniques and those not invented yet are believed to be suitable. The solids separated from this process are in the second solid stream 10. Stream 9 is noted and is the second liquid stream.

Figure 7:
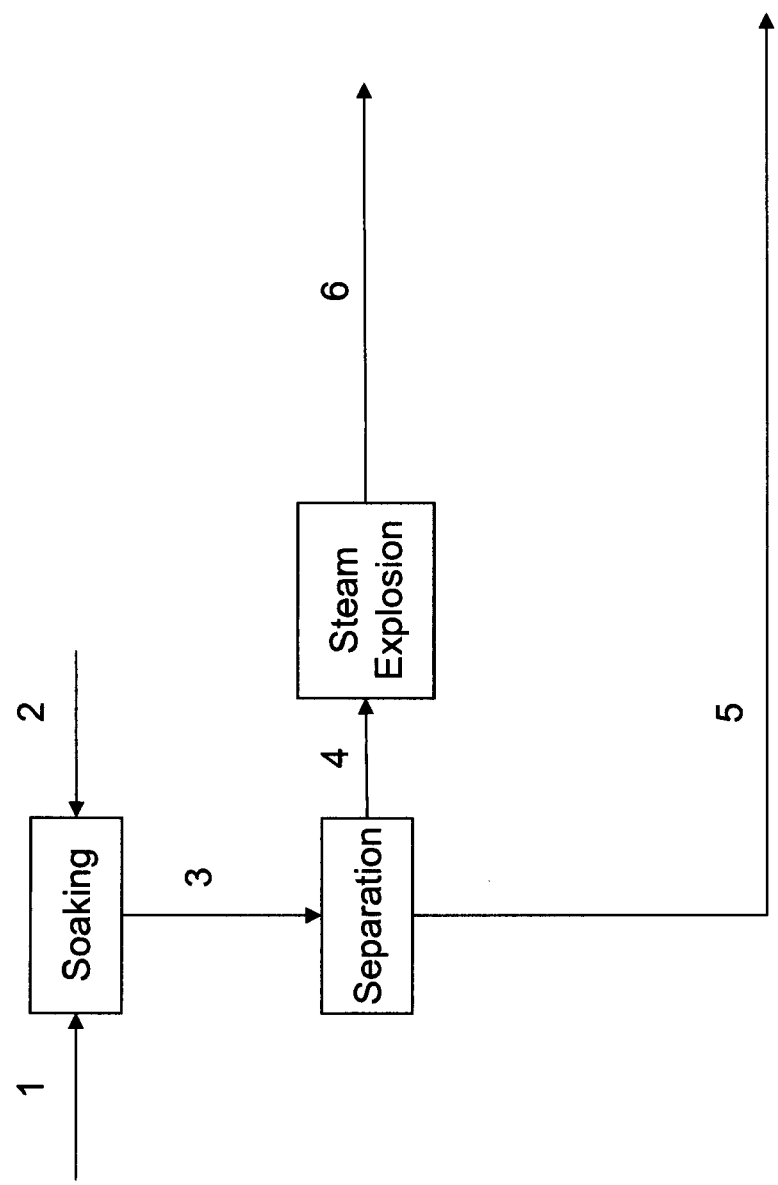
FIG. 7 is a schematic of a seventh, embodiment of the process.
Figure 8:
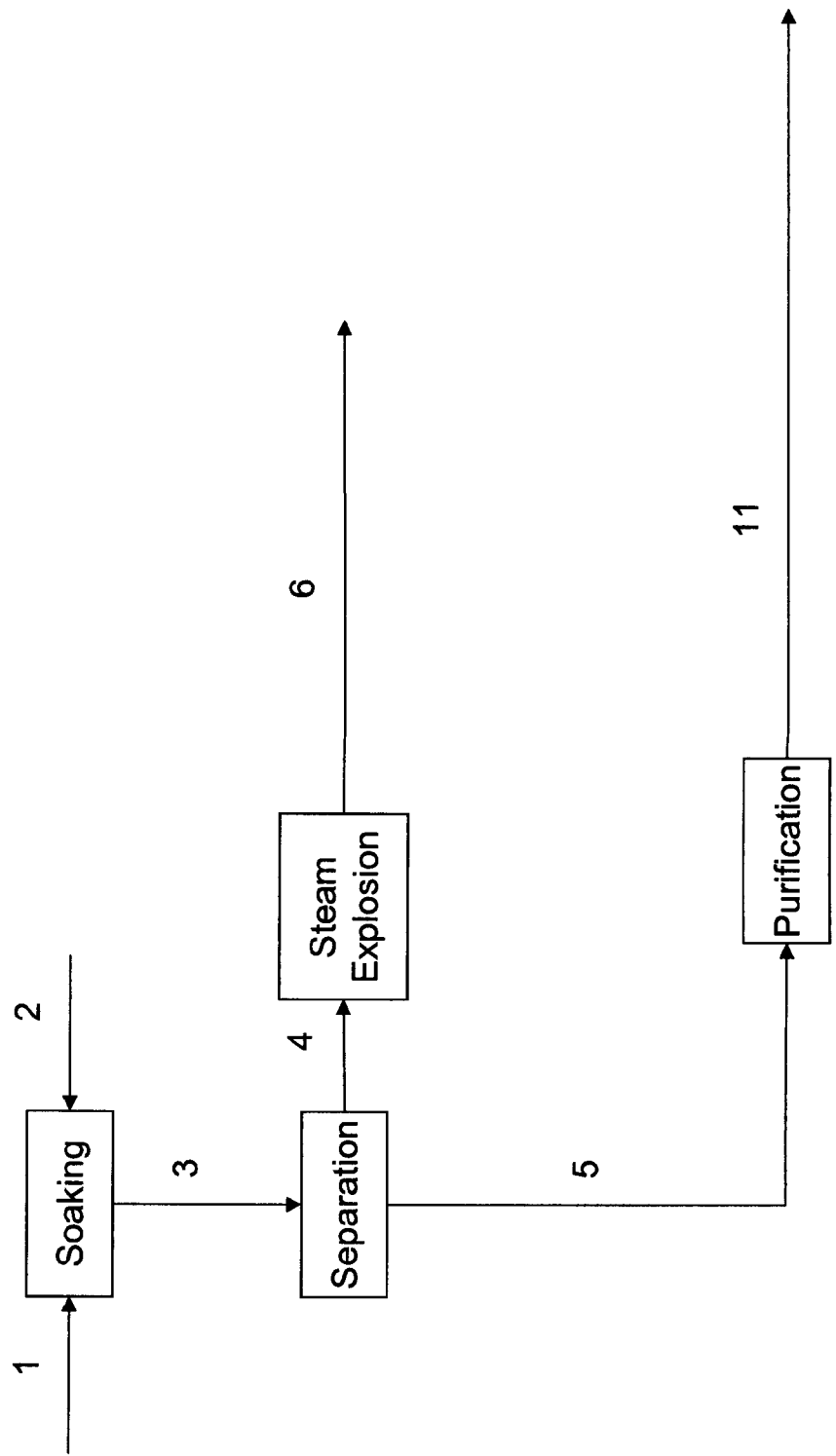
FIG. 8 is a schematic of an eighth embodiment of the process.

The embodiment in FIG. 7 shows the process without the optional washing and separation of the liquid from the steam exploded material.

The liquid of the first liquid stream is then combined with the solids of the second solid stream to form stream 20.

The product of this process is noted as very specific, in that one or any combination of the following improvements are achieved:
A) the levels of inhibitors and undesirable products to the next steps (e.g. enzymatic hydrolysis, fermentation, final product separation) with the various materials in the biomass are much lower than other processes;
B) the global hemicellulose solubilization yield is higher than other process;
C) the biomass de-structuring is improved with respect to other process.

The novel compositions of this process can be characterized on the basis of their C5, C6 and furfural amounts. To avoid dilution effects, the expression of the ratio C5's/C6's and furfural to the C5's plus C6's, with furfural being present is sufficient to characterize the new compositions.

The total C5's in the composition is the sum of arabinan and xylan in the composition which includes the monomers, dimers, oligomers and polymers of arabinose and xylose in the liquid and solid of the composition. The total C6's in the composition is the glucan content which includes the monomers, dimers, oligomers and polymers in the liquid and solid.

As known in the literature, a typical steam exploded biomass will have a ratio of furfural to [C5's plus C6's]×10000 of at least 50, with a ratio of C5's to C6's greater than 0.55. As shown in the experimental streams from Tables 13 and 14, the process described herein is capable of producing a steam exploded product with a furfural content greater than 0, that is always present, but having a ratio of furfural to (C5's plus C6's)×10000 of less than 60. Therefore a composition having a ratio of C5's to C6's in the range of 0.45 to 0.54, and a ratio of furfural to [C5's plus C6's]×10000 between 0 and 60, or more preferably 0 and 50, or more preferably 0 and 30 is contemplated. It is also noted in Tables 13 and 14 that the other novel feature is that the product is low in C5's which also reduces the furfural content.

As can be seen from the Tables 13 and 14, these compositions from the steam explosion can be characterized as always having furfural and having the ratio of C5's to C6's less than 0.45 and a ratio of furfural to C5's plus C6's×10000 of less than 40, or more preferably, a ratio of C5's to C6's less than 0.45 and a ratio of furfural to C5's plus C6's×10000 of less than 15, or more preferably the ratio of C5's to C6's less than 0.45 and a ratio of furfural to C5's plus C6's×10000 of less than 10; or more preferably a ratio of C5's to C6's less than 0.40 and a ratio of furfural to C5's plus C6's×10000 of less than 40, or even more preferably a ratio of C5's to C6's less than 0.40 and a ratio of furfural to C5's plus C6's×10000 of less than 9, the ratio of C5's to C6's less than 0.35 and a ratio of furfural to C5's plus C6's×10000 of less than 10, or even more preferably, the ratio of C5's to C6's less than 0.30 and a ratio of furfural to C5's plus C6's×10000 of less than 7.

As also shown in Tables 13 and 14, the composition of the liquid stream is also unique and can be described as always having furfural and having a ratio of C5's to C6's greater than 4.0 and a ratio of furfural to C5's plus C6's×10000 of less than 80, or more preferably a ratio of C5's to C6's greater than 4.0 and a ratio of furfural to C5's plus C6's×10000 of less than 60, or even more preferably a ratio of C5's to C6's greater than 4.0 and a ratio of furfural to C5's plus C6's×10000 of less than 30, or a broader range of a ratio of C5's to C6's greater than 3.0 and a ratio of furfural to C5's plus C6's×10000 of less than 160.

Also contemplated is the composition of the liquid stream always having furfural and having a ratio of C5's to C6's greater than 1.0 and a ratio of furfural to C5's plus C6's×10000 of less than 800, or more preferably a ratio of C5's to C6's greater than 1.0 and a ratio of furfural to C5's plus C6's×10000 of less than 700, or even more preferably a ratio of C5's to C6's greater than 1.0 and a ratio of furfural to C5's plus C6's×10000 of less than 400, or the narrower broad range of a ratio of C5's to C6's greater than 1.0 and a ratio of furfural to C5's plus C6's×10000 of less than 300.

Figure 2:
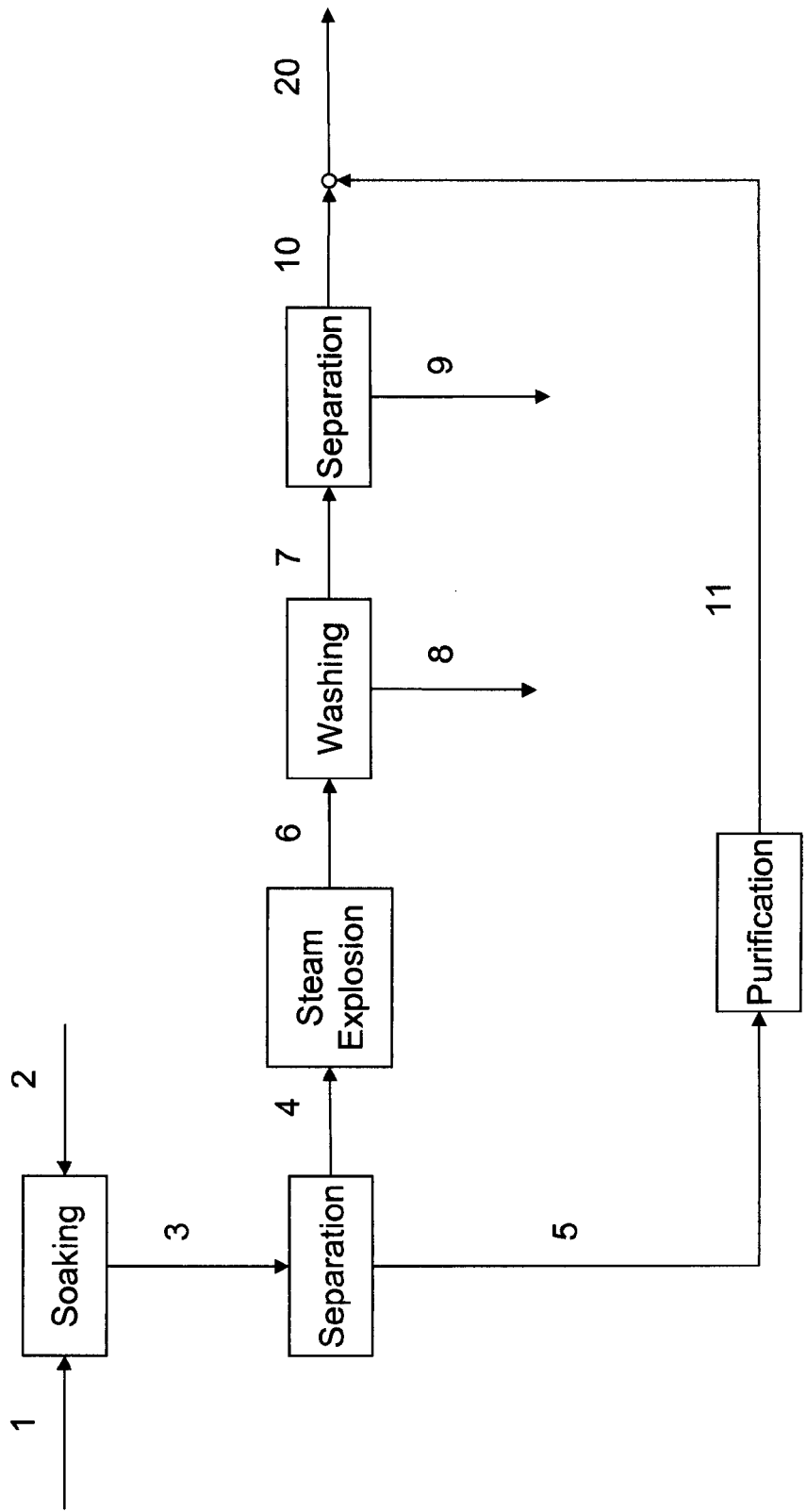
FIG. 2 is a schematic of a second embodiment of the process.

A further progression of the process, FIG. 2, is to purify the first liquid stream to remove even more of the inhibitors such as the acetic acid, formic acid, levulinic acid, furfural, 5-HMF, phenolic compounds and, more in general, any undesirable product which may be formed during previous steps. Some of these compounds are removable by flashing, which is the preferred method in order to exploit the temperature and pressure of the stream after pressing.

For example, the first liquid stream (temperature: 185° C., saturated liquid phase) was flashed using conventional conditions to atmospheric pressure. For 100 grams of the feed stream, having 0.1 grams of furfural, 2 grams of acetic acid, 0.1 grams of formic acid and 82 grams of water flashed, 0.045 grams of furfural, 0.024 grams of acetic acid, 0.06 grams of formic acid and 14.7 grams of water were removed. This means that 45% of furfural, 12% of acetic acid, 6% of formic acid and 17% of the water were removed without any additional operating costs and without any loss in sugars.

Another advantage of flash step is that sugars in the purified liquid stream 11 are concentrated.

In the flash process, the pressure from the pressing in the separation would preferably be preserved until the material is passed to flash tank and the volatiles removed. The purification of the first liquid stream can again be done by any other known techniques (e.g. steam stripping) and likely some which have yet been invented. This first purified material can be found in the first purified material stream 11 and then combined with the second solids stream 10.

Figure 3:
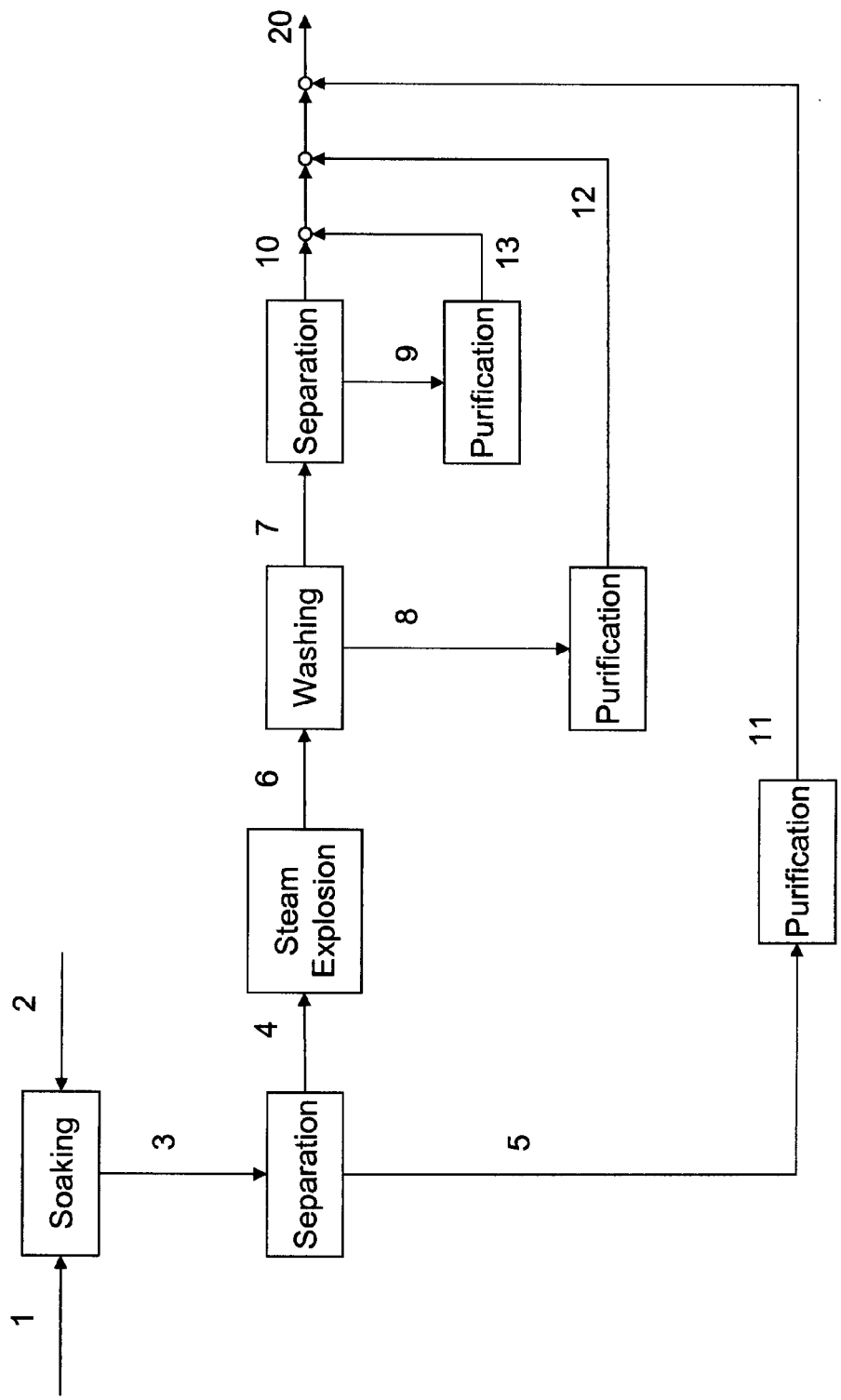
FIG. 3 is a schematic of a third embodiment of the process.

An even further refinement is depicted in FIG. 3, which is to purify the optional wash effluent, the third liquid stream 8, into a second purified liquid stream 12, and then combine it with the second solid stream 10. Due to the nature of the volatiles, steam stripping using conventional or not conventional methods is believed to be the preferred approach, even if any other method or known techniques and likely some which have yet been invented can be utilized.

If possible, on the basis of its composition, steam coming from steam explosion is preferably used to carry out steam stripping.

Similarly, referring to FIG. 3, one could purify the second liquid stream 9, to create a second purified liquid in the second purified liquid stream 13 and combine it with the material in the second solid stream 10. Again, given the known attributes, steam stripping is believed to be the preferred solution.

Figure 4:
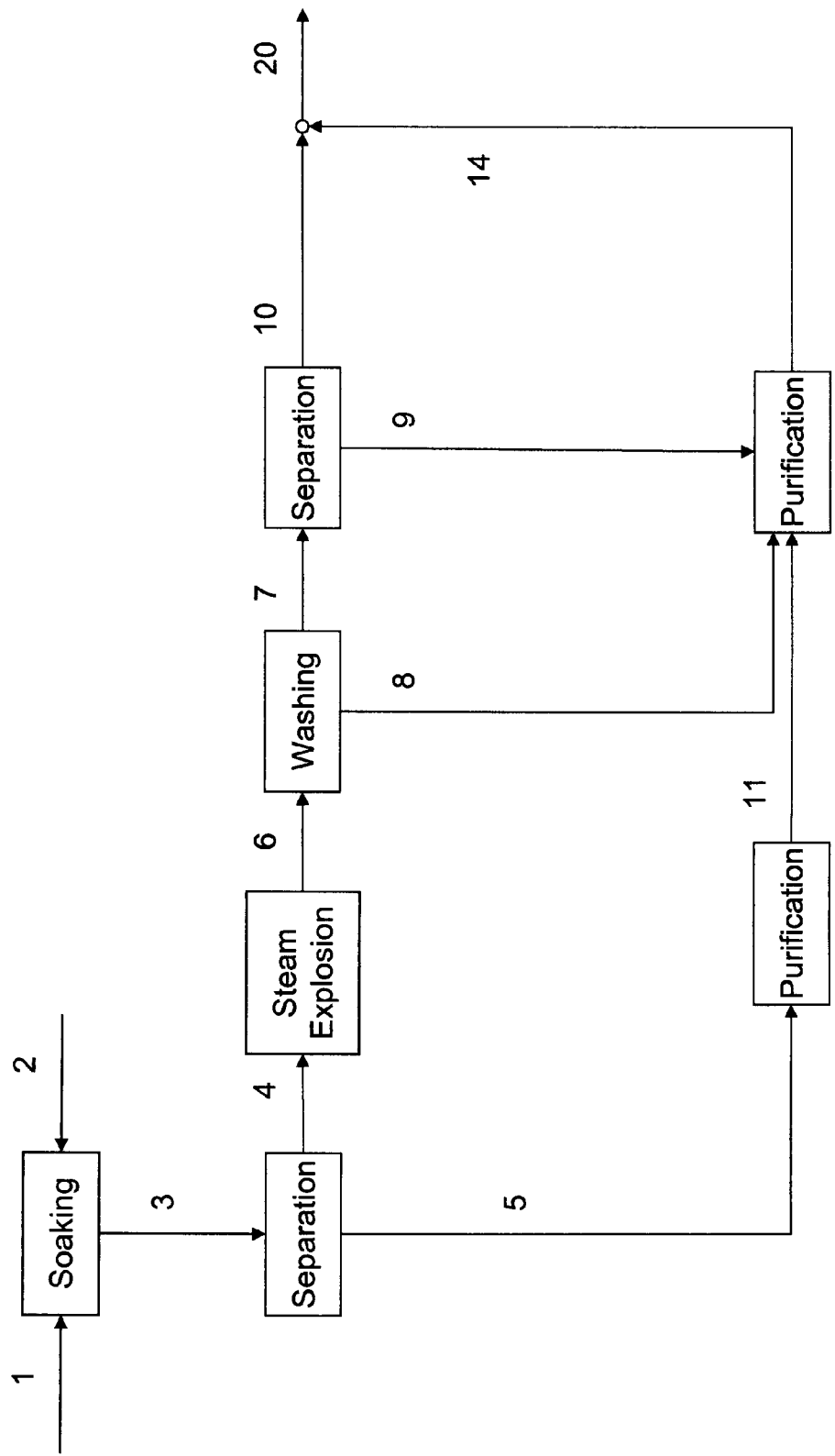
FIG. 4 is a schematic of a fourth embodiment of the process.

Since steam stripping is common, it is believed that a preferred embodiment of the process steam strip the second and third liquid streams in the same unit. It is also believed that steam stripping is also preferred for the first purified liquid stream, generally after flashing. Therefore another embodiment is FIG. 4 where the liquid streams are purified in the same unit, preferably steam stripping to product the purified stream 14 which is then combined with the second solid stream 10.

If possible, on the basis of its composition, steam coming from steam explosion may be used to carry out any steam stripping.

For example, in a process as represented in FIG. 2, in which purification step consists of an atmospheric flash step of the first liquid stream 5 and a subsequent steam stripping step of the liquid resulting, performed utilizing all the steam produced by the steam explosion, it results that 30% of water, 80% of acetic acid, 85% of furfural and 65% of formic acid contained in the first liquid stream 5 are removed.

Figure 5:
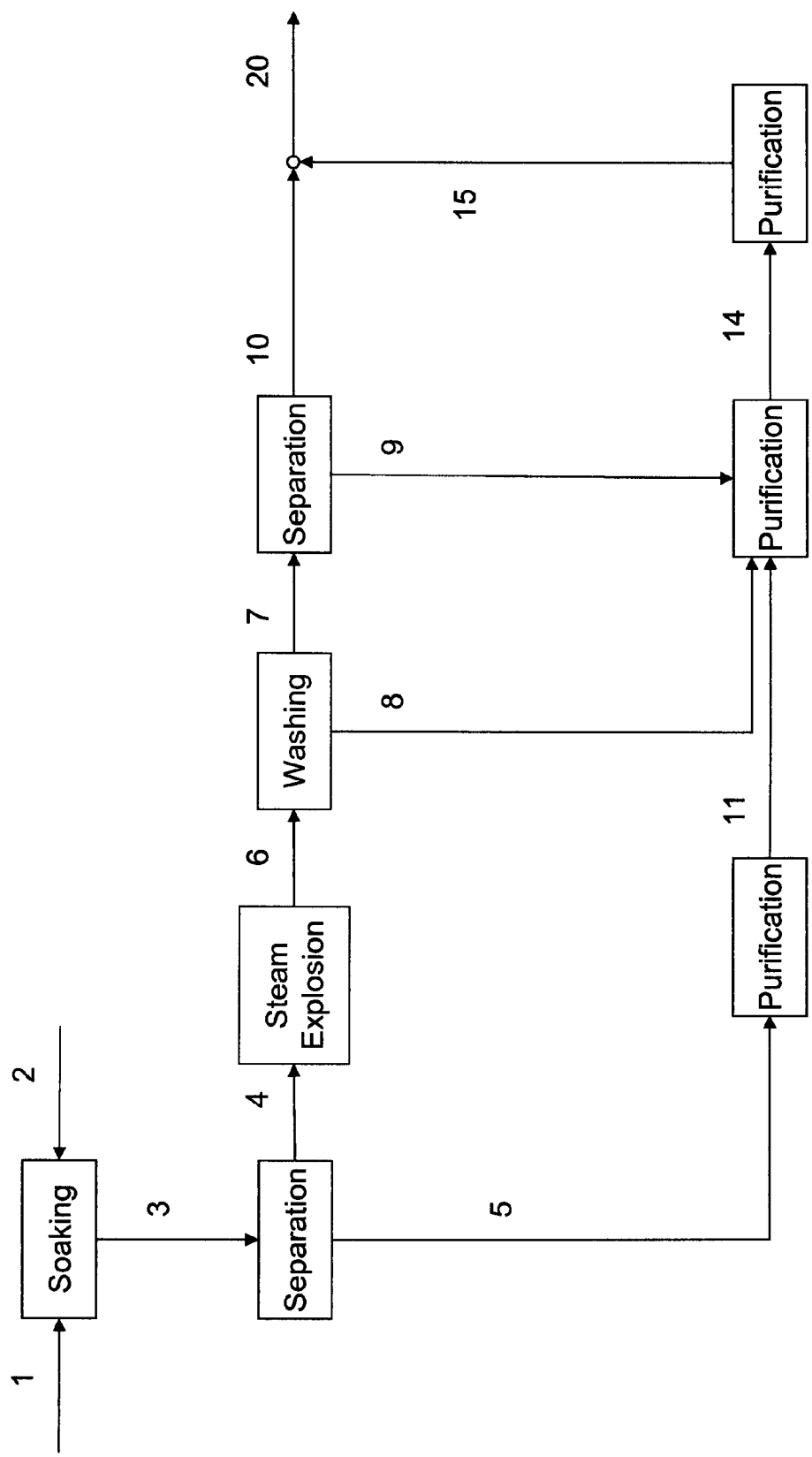
FIG. 5 is a schematic of a fifth embodiment of the process.
Figure 6:
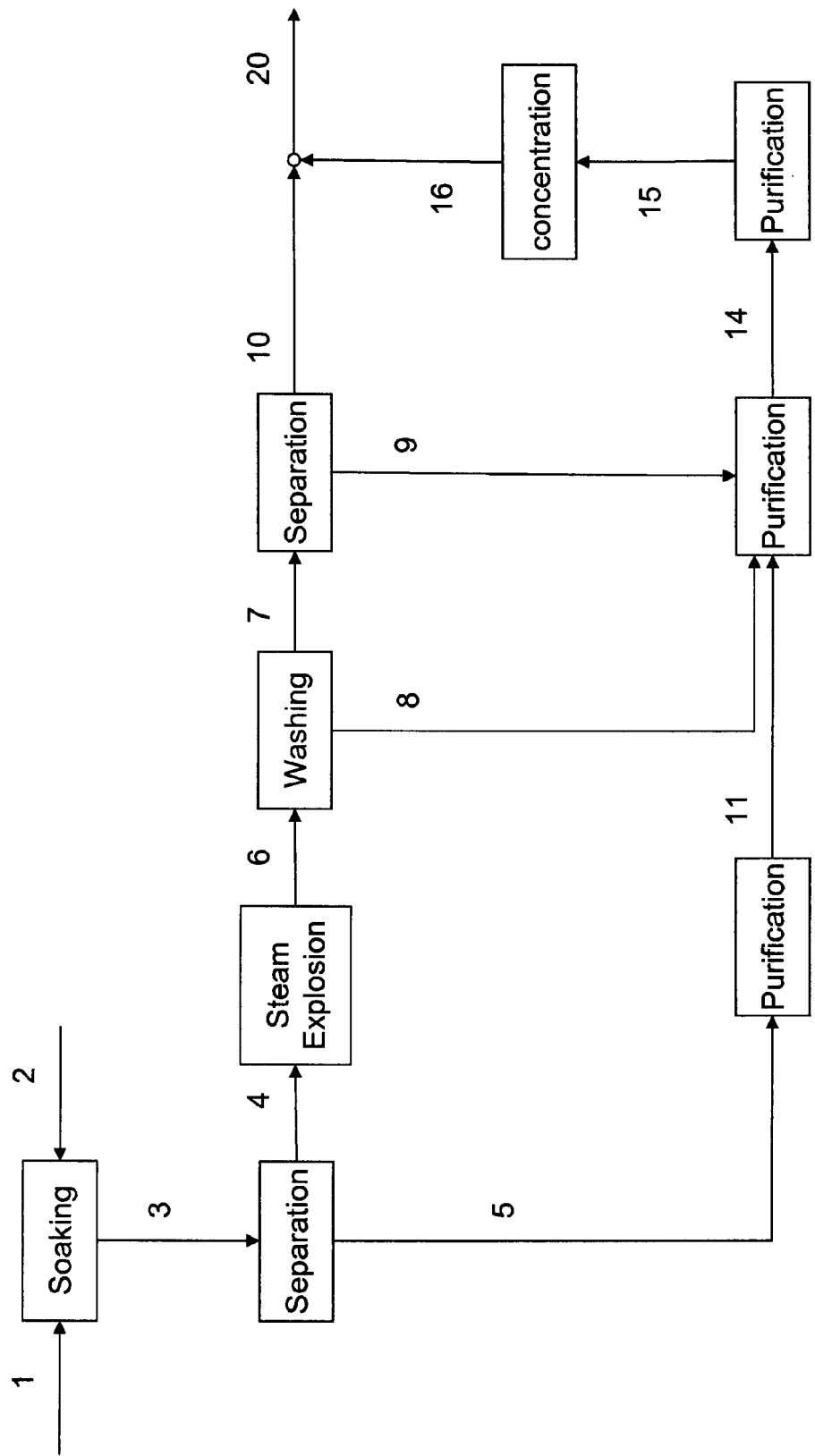
FIG. 6 is a schematic of a sixth embodiment of the process.

Should further purification be needed depending upon the feedstock and type of biomass, the purified stream 14, can be further purified with another process FIG. 5, such as activated charcoal, activated carbon, molecular sieves or membranes to produce stream 15. Because the purified stream is expected to have a large water content, it is believed desirable to concentrate the hydrolysis reactants and remove the water, therefore a concentration step is believed helpful for the preferred embodiment, FIG. 6. The water concentration step can be any one of the know techniques such as boiling, crystallization, and the like. During concentration step, there is some removal of volatile inhibitors. After the concentration step, stream 16 is combined with the materials in stream 10.

As shown in the data below, the various steps of this process have increased the efficiency of hydrolysis reaction.

Discussion

The superiority of the pretreatment can be seen by comparing the results presented in the working examples 5-6 compared to control examples 1, 2, 3, and 4

The amount of inhibitors generated from xylan fraction in the pretreatment is considerably lower then those generated in continuous steam explosion process.

Using *Arundo* only 1.3% of xylans present in raw material are degraded to inhibitors compound (Example 5) with the pretreatment, while in steam explosion process a 19.3% (Example 1) and 63.8% (Example 2) are degraded to inhibitors compound.

A similar behaviour is observed for glucan degradation using *Arundo*. Only 0.1% of glucans present in raw material are degraded to inhibitors compound (Example 5) with the pretreatment, while in steam explosion process a 1.9% (Example 1) and 4.5% (Example 2) are degraded to inhibitors compound.

Using sorghum only 0.97% of xylans present in raw material are degraded to inhibitors compound (Example 6) with the pretreatment, while in steam explosion process a 61.7% (Example 3) and 94.9% (Example 4) are degraded to inhibitors compound.

A similar behaviour is observed for glucan degradation using *Arundo*. Only 0.1% of glucans present in raw material are degraded to inhibitors compound (Example 6) with the pretreatment, while in steam explosion process an 8.0% (Example 3) and 9.5% (Example 4) are degraded to inhibitors compound.

The overall yield of solubilisation of fermentable sugar (sum of solubilized xylan and glucans) is another advantage of the pretreatment.

An overall yield in terms of fermentable sugar (sum of solubilized xylan and glucans) of 91.2% is obtained with sorghum after enzymatic hydrolysis with the pretreatment (Example 5) that is considerably higher with the values obtained with traditional steam explosion (65.9% in Example 1, and 69.0% in Example 2).

An overall yield in terms of fermentable sugar (sum of solubilized xylan and glucans) of 91.3% is obtained with *Arundo* after enzymatic hydrolysis with the pretreatment (Example 6) that is considerably higher with the values obtained with traditional steam explosion (56.0% in Example 3, and 50.6% in Example 4)

EXPERIMENTAL SUMMARY

*Arundo* and *sorghum* were submitted to different pretreatment process. Traditional continuous steam explosion was compared with the pretreatment consisting of a soaking process and a subsequent steam explosion process.

In the pretreatment the liquid fraction generated from the soaking process is recycled as a unique stream.

In the soaking process the solubilisation occurs of the major part of the hemi cellulosic fraction. A low inhibitor amount is generated in this process due to the milder operational condition.

The soaked material is then submitted to a pressing process in order to remove the liquid fraction (about 62%)

The solid fraction is then submitted to steam explosion treatment in which occurs the solubilisation of the remaining hemicellulose and the de-structuring of cellulose fraction.

The liquid fraction generated in the soaking process is submitted to refining process and then recycled to the steam exploded material.

The pretreatment lead to less inhibitor in the stream leaving pretreatment section with consequent lower loss of fermentable sugar when compared with traditional steam explosion pretreatment, and increase enzymatic accessibility of the pretreated material.

Pretreated material from traditional steam explosion and the pretreatment were submitted to enzymatic hydrolysis in order to evaluate the enzymatic accessibility.

The overall yield of the process was calculated starting from the composition of raw entering the pretreatment process, taking into account the material balance of the process and the enzymatic hydrolysis yield on glucan and xylan.

Example 1

*Arundo* has the following composition: 37.5% glucans, 19.3% xylans, 5.8% acetyl groups, 22.6% Klason lignin 6.3% ash, 8.5% extractives.

*Arundo* was submitted to continuous steam explosion (Stake Tech reactor) at 200° C. for 6 minutes. This pretreatment lead to a solubilisation of 70.6% of xylan and 8.6% of glucan. A 19.3% of xylan were degraded to inhibitor compounds (furfural and other degradation product), and 1.9% of glucans were degraded to inhibitors compounds (HMF and formic acid)

An amount of pretreated material which composition can be summarized in solvent, soluble solid, insoluble solid, is added to a laboratory fermenter. Solvent (water, buffer, antibacterial solution) and catalyst solution are added to this material in order to reach a total solid content of 7.5%. Catalysts solution is calculated to have an activity of 60 FPU/g glucans and 109 FXU/g xylan for pretreated *Arundo*.

The composition of the stream entering the enzymatic hydrolysis is shown in Table 1

TABLE 1

Composition of the stream entering enzymatic hydrolysis

| | Stream entering Enzymatic hydrolysis (g) *Arundo* |
|---|---|
| Total | 1000.0 |
| Water | 925.0 |
| Total solid | 75.0 |
| Insoluble solid | 55.2 |
| Glucan | 25.7 |
| Xylan | 4.2 |
| Acetyl group | 3.0 |
| Lignin | 18.9 |
| Ash | 3.3 |
| Extractives | 0.0 |
| Soluble solid | 19.8 |
| Extractives | 6.43 |
| Glucan | 0.26 |
| Xylan | 0.75 |
| Acetyl group | 2.96 |
| Acetic acid | 2.17 |
| 5-HMF | 0.11 |
| Furfural | 0.22 |
| Formic acid | 0.00 |
| Glucolygomers as glucan | 1.65 |
| Xyloolygomers as xylan | 6.74 |

After enzymatic hydrolysis, the process liquid and solid fraction were analyzed in order to quantify the yield of glucan and xylan solubilisation. In enzymatic hydrolysis process glucan solubilisation yield was 71%, while xylan solubilisation yield was 84%.

The global yield of the process was calculated starting from the composition of raw entering the pretreatment process, taking into account the material balance of the process and the enzymatic hydrolysis yield on glucan and xylan.

A process solubilisation yield of 69.3% was calculated for glucan, while a process solubilisation yield of 59.3% was calculated for xylan. A global solubilisation yield of 65.9%, referred to the sum of glucan and xylan present in the raw material is calculated in this process. The global yield for *Arundo* is in Table 2

TABLE 2

Enzymatic hydrolysis and process yield of glucan and xylan
*Arundo*

|  | STEAM EXPLOSION (200° C., 6 min) |
|---|---|
| Enzymatic hydrolysis yield glucans (%) | 71 |
| Enzymatic hydrolysis yield xylans (%) | 84 |
| Glucan Process yield (%) | 69.3 |
| Xylan process yield (%) | 59.3 |
| $FPU/g_{cellulose}$ | 60 |
| $FPU/g_{xylans}$ | 220 |

Example 2

*Arundo* has the following composition: 37.5% glucans, 19.3% xylans, 5.8% acetyl groups, 22.6% Klason lignin 6.3% ash, 8.5% extractives.

*Arundo* was submitted to continuous steam explosion (Stake Tech reactor) at 215° C. for 6 minutes. This pretreatment lead to a solubilisation of 90.8% of xylan and 7.1% of glucan. A 63.8% of xylan were degraded to inhibitor compounds (furfural and other degradation product), and 4.5% of glucans were degraded to inhibitors compounds (HMF and formic acid)

An amount of pretreated material which composition can be summarized in solvent, soluble solid, insoluble solid, is added to a laboratory fermenter. Solvent (water, buffer, antibacterial solution) and catalyst solution are added to this material in order to reach a total solid content of 7.5%. Catalysts solution is calculated to have an activity of 60 FPU/g glucans and 248 FXU/g xylan for pretreated *Arundo*.

The composition of the stream entering the enzymatic hydrolysis is shown in Table 3

TABLE 3

Composition of the stream entering enzymatic hydrolysis

|  | Stream entering Enzymatic hydrolysis (g) *Arundo* |
|---|---|
| Total | 1000.0 |
| Water | 925.0 |
| Total solid | 75.0 |
| Insoluble solid | 53.0 |
| Glucan | 26.1 |
| Xylan | 1.3 |
| Acetyl group | 1.8 |
| Lignin | 20.2 |
| Ash | 3.6 |
| Extractives | 0.0 |
| Soluble solid | 22.0 |
| Extractives | 6.4 |
| Glucan | 0.3 |
| Xylan | 0.8 |
| Acetyl group | 1.6 |
| Acetic acid | 3.6 |
| 5-HMF | 0.0 |
| Furfural | 0.3 |

TABLE 3-continued

Composition of the stream entering enzymatic hydrolysis

|  | Stream entering Enzymatic hydrolysis (g) *Arundo* |
|---|---|
| Formic acid | 0.1 |
| Glucolygomers as glucan | 0.5 |
| Xyloolygomers as xylan | 3.6 |

After enzymatic hydrolysis, the process liquid and solid fraction were analyzed in order to quantify the yield of glucan and xylan solubilisation. In enzymatic hydrolysis process glucan solubilisation yield was 82%, while xylan solubilisation yield was 99%.

The global yield of the process was calculated starting from the composition of raw material entering the pretreatment process, taking into account the material balance of the process and the enzymatic hydrolysis yield on glucan and xylan.

A process solubilisation yield of 87.8% was calculated for glucan, while a process solubilisation yield of 35% was calculated for xylan. A global solubilisation yield of 69.0%, referred to the sum of glucan and xylan present in the raw material is calculated in this process.

The global yield for *Arundo* is in Table 4

TABLE 4

Enzymatic hydrolysis and process yield of glucan and xylan
*Arundo*

|  | STEAM EXPLOSION (215° C., 6 min) |
|---|---|
| Enzymatic hydrolysis yield glucans (%) | 92 |
| Enzymatic hydrolysis yield xylans (%) | 99 |
| Glucan Process yield (%) | 87.8 |
| Xylan process yield (%) | 35.0 |
| $FPU/g_{cellulose}$ | 60 |
| $FPU/g_{xylans}$ | 220 |

Example 3

Fiber sorghum has the following composition: 35.8% glucans, 20.0% xylans, 5.61% acetyl groups, 17.3% Klason lignin 6.4% ash, 14.8% extractives.

Chopped sorghum was submitted to continuous steam explosion (Stake Tech reactor) at 200° C. for 6 minutes. This pretreatment lead to a solubilisation of 86.6% of xylan and 25.5% of glucan. A 61.7% of xylan were degraded to inhibitor compounds (furfural and other degradation product), and 8.0% of glucans were degraded to inhibitors compounds (HMF and formic acid)

An amount of pretreated material which composition can be summarized in solvent, soluble solid, insoluble solid, is added to a laboratory fermenter. Solvent (water, buffer, antibacterial solution) and catalyst solution are added to this material in order to reach a total solid content of 7.5%. Catalysts solution is calculated to have an activity of 60 FPU/g glucans and 220 FXU/g xylan for pretreated *Sorghum*.

The composition of the stream entering the enzymatic hydrolysis is shown in Table 5.

TABLE 5

Composition of the stream entering enzymatic hydrolysis

| | Stream entering Enzymatic hydrolysis (g) Sorghum |
|---|---|
| Total | 1000.0 |
| Water | 925.0 |
| Total solid | 75.0 |
| Insoluble solid | 42 |
| Glucan | 20.0 |
| Xylan | 2.0 |
| Acetyl group | 0.5 |
| Lignin | 17.1 |
| Ash | 2.4 |
| Extractives | 0.0 |
| Soluble solid | 33.0 |
| Extractives | 11.1 |
| Glucan | 0.1 |
| Xylan | 0.5 |
| Acetyl group | 0.2 |
| Acetic acid | 1.8 |
| 5-HMF | 0.1 |
| Furfural | 0.2 |
| Formic acid | 0.6 |
| Glucolygomers as glucan | 4.6 |
| Xyloolygomers as xylan | 3.2 |

After enzymatic hydrolysis, the process liquid and solid fraction were analyzed in order to quantify the yield of glucan and xylan solubilisation. In enzymatic hydrolysis process glucan solubilisation yield was 77%, while xylan solubilisation yield was 85%.

The global yield of the process was calculated starting from the composition of raw material (Table 1) entering the pretreatment process, taking into account the material balance of the process and the enzymatic hydrolysis yield on glucan and xylan.

A process solubilisation yield of 70.8% was calculated for glucan, while a process solubilisation yield of 32.1% was calculated for xylan. A global solubilisation yield of 56.0%, referred to the sum of glucan and xylan present in the raw material is calculated in this process.

The global yield for sorghum is in Table 6

TABLE 6

Enzymatic hydrolysis and process yield of glucan and xylan

| | Sorghum STEAM EXPLOSION (200° C., 6 min) |
|---|---|
| Enzymatic hydrolysis yield glucans (%) | 77 |
| Enzymatic hydrolysis yield xylans (%) | 85 |
| Glucan Process yield (%) | 70.8 |
| Xylan process yield (%) | 32.1 |
| $FPU/g_{cellulose}$ | 60 |
| $FPU/g_{xylans}$ | 220 |

Example 4

Fiber sorghum has the following composition: 35.8% glucans, 20.0% xylans, 5.61% acetyl groups, 17.3% Klason lignin 6.4% ash, 14.8% extractives.

Chopped sorghum was submitted to continuous steam explosion (Stake Tech reactor) at 207° C. for 6 minutes. This pretreatment lead to a solubilisation of 94.9% of xylan and 23.4% of glucan. A 86.3% of xylan were degraded to inhibitor compounds (furfural and other degradation product), and 9.5% of glucans were degraded to inhibitors compounds (HMF and formic acid)

An amount of pretreated material which composition can be summarized in solvent, soluble solid, insoluble solid, is added to a laboratory fermenter. Solvent (water, buffer, antibacterial solution) and catalyst solution are added to this material in order to reach a total solid content of 7.5%. Catalysts solution is calculated to have an activity of 60 FPU/g glucans and 248 FXU/g xylan for pretreated Sorghum.

The composition of the stream entering the enzymatic hydrolysis is shown in Table 7.

TABLE 7

Composition of the stream entering enzymatic hydrolysis

| | Stream entering Enzymatic hydrolysis (g) Sorghum |
|---|---|
| Total | 1000.0 |
| Water | 925.0 |
| Total solid | 75.0 |
| Insoluble solid | 42 |
| Glucan | 26.1 |
| Xylan | 1.3 |
| Acetyl group | 1.8 |
| Lignin | 20.2 |
| Ash | 3.6 |
| Extractives | 0.0 |
| Soluble solid | 33.0 |
| Extractives | 6.4 |
| Glucan | 0.3 |
| Xylan | 0.8 |
| Acetyl group | 1.6 |
| Acetic acid | 3.6 |
| 5-HMF | 0.0 |
| Furfural | 0.3 |
| Formic acid | 0.1 |
| Glucolygomers as glucan | 0.5 |
| Xyloolygomers as xylan | 3.6 |

After enzymatic hydrolysis, the process liquid and solid fraction were analyzed in order to quantify the yield of glucan and xylan solubilisation. In enzymatic hydrolysis process glucan solubilisation yield was 79%, while xylan solubilisation yield was 99%.

The global yield of the process was calculated starting from the composition of raw material entering the pretreatment process, taking into account the material balance of the process and the enzymatic hydrolysis yield on glucan and xylan.

A process solubilisation yield of 71.5% was calculated for glucan, while a process solubilisation yield of 13.4% was calculated for xylan. A global solubilisation yield of 50.60%, referred to the sum of glucan and xylan present in the raw material is calculated in this process.

The global yield for sorghum is in Table 8.

TABLE 8

Enzymatic hydrolysis and process yield of glucan and xylan

| | Sorghum STEAM EXPLOSION (207° C., 6 min) |
|---|---|
| Enzymatic hydrolysis yield glucans (%) | 79 |
| Enzymatic hydrolysis yield xylans (%) | 99 |
| Glucan Process yield (%) | 71.5 |
| Xylan process yield (%) | 13.4 |
| $FPU/g_{cellulose}$ | 60 |
| $FPU/g_{xylans}$ | 248 |

Example 5

*Arundo* has the following composition: 37.5% glucans, 19.3% xylans, 5.8% acetyl groups, 22.6% Klason lignin 6.3% ash, 8.5% extractives.

*Arundo* was submitted to batch soaking process for 100 min at 160° C., in which occurred a first solubilisation of the raw material. A solid phase and a liquid phase were generated in this process. The solid phase was submitted to a batch steam explosion pretreatment at 200° C. for 8 minutes. The liquid phase generated in the soaking process was then recycled to the steam exploded material.

This pretreatment lead to a solubilisation of 81.2% of xylan and 3.7% of glucan. A 1.3% of xylan were degraded to inhibitor compounds (furfural and other degradation product), and 0.1% of glucans were degraded to inhibitors compounds (HMF and formic acid).

An amount of pretreated material which composition can be summarized in solvent, soluble solid, insoluble solid, is added to a laboratory fermenter. Solvent (water, buffer, antibacterial solution) and catalyst solution are added to this material in order to reach a total solid content of 7.5%. Catalysts solution is calculated to have an activity of 34 FPU/g glucans and 68 FXU/g xylan for pretreated *Arundo*.

The composition of the stream entering enzymatic hydrolysis is reported in table 9.

TABLE 9

Composition of the stream entering enzymatic hydrolysis

|  | Stream entering Enzymatic hydrolysis (g) *Arundo* |
|---|---|
| Total | 1000.0 |
| Water | 925.0 |
| Total solid | 75.0 |
| Insoluble solid | 42.7 |
| Glucan | 26.7 |
| Xylan | 2.5 |
| Galactan | 0.4 |
| Arabinan | 0.2 |
| Acetyl group | 0.8 |
| Lignin | 10.8 |
| Ash | 1.2 |
| Extractives | 0.0 |
| Soluble solid | 32.3 |
| Glucan | 0.1 |
| Xylan | 1.2 |
| Galactan | 0.1 |
| Arabinan | 0.3 |
| Acetic acid | 1.0 |
| HMF | 0.0 |
| Furfural | 0.1 |
| Glucolygomers as glucan | 0.9 |
| Xyloolygomers as xylan | 9.4 |
| Galactolygomers as galactan | 0.1 |
| Arabinolygomers as arabinan | 0.3 |
| Acetyl groups | 1.2 |
| Extractives | 6.4 |

The global yield of the process was calculated starting from the composition of raw material (Table 1) entering the pretreatment process, taking into account the material balance of the process and the enzymatic hydrolysis yield on glucan and xylan A process solubilisation yield of 87.4% was calculated for glucan, while a process solubilisation yield of 97.5% was calculated for xylan. A global solubilisation yield of 91.2%, referred to the sum of glucan and xylan present in the raw material is calculated in this process.

The global yield for *Arundo* is in Table 10

TABLE 10

Enzymatic hydrolysis and process yield of glucan and xylan

|  | *Arundo* Soak (160° C., 100 min) + Stm Exp (200° C., 8 min) |
|---|---|
| Enzymatic hydrolysis yield glucans (%) | 87.6 |
| Enzymatic hydrolysis yield xylans (%) | 98.8 |
| Glucan Process yield (%) | 87.4 |
| Xylan Process yield (%) | 97.5 |
| $FPU/g_{cellulose}$ | 34 |
| $FPU/g_{xylans}$ | 68 |

Example 6

Fiber sorghum has the following composition: 35.8% glucans, 20.0% xylans, 5.61% acetyl groups, 17.3% Klason lignin, 6.4% ash, 14.8% extractives Fiber sorghum was submitted to batch soaking process for 25 min at 180° C., in which occurred a first solubilisation of the raw material. A solid phase and a liquid phase were generated in this process. The solid phase was submitted to a batch steam explosion pretreatment at 200° C. for 8 minutes. The liquid phase generated in the soaking process was then recycled to the steam exploded material.

This pretreatment lead to a solubilisation of 63.6% of xylan and 6.3% of glucan. A 0.97% of xylan were degraded to inhibitor compounds (furfural and other degradation product), and 0.1% of glucans were degraded to inhibitors compounds (HMF and formic acid).

An amount of pretreated material which composition can be summarized in solvent, soluble solid, insoluble solid, is added to a laboratory fermenter. Solvent (water, buffer, antibacterial solution) and catalyst solution are added to this material in order to reach a total solid content of 7.5%. Catalysts solution is calculated to have an activity of 34 FPU/g glucans and 59 FXU/g xylan for pretreated sorghum.

The composition of the stream entering enzymatic hydrolysis is reported in table 11.

TABLE 11

Composition of the stream entering enzymatic hydrolysis

|  | Stream entering Enzymatic hydrolysis (g) *Sorghum* |
|---|---|
| Total | 1000.0 |
| Water | 925.0 |
| Total solid | 75.0 |
| Insoluble solid | 42.4 |
| Glucan | 25.0 |
| Xylan | 5.9 |
| Galactan | 0.0 |
| Arabinan | 0.4 |
| Acetyl group | 1.1 |
| Lignin | 8.9 |
| Ash | 1.1 |
| Extractives | 0.0 |
| Soluble solid | 32.6 |
| Glucan | 0.1 |
| Xylan | 0.3 |
| Galactan | 0.0 |
| Arabinan | 0.4 |
| Acetic acid | 0.9 |
| HMF | 0.0 |
| Furfural | 0.1 |

TABLE 11-continued

Composition of the stream entering enzymatic hydrolysis

|  | Stream entering Enzymatic hydrolysis (g) Sorghum |
|---|---|
| Glucolygomers as glucan | 1.3 |
| Xyloolygomers as xylan | 7.1 |
| Galactolygomers as galactan | 0.3 |
| Arabinolygomers as arabinan | 0.5 |
| Acetyl groups | 0.8 |
| Extractives | 11.1 |

The global yield of the process was calculated starting from the composition of raw material (Table 1) entering the pre-treatment process, taking into account the material balance of the process and the enzymatic hydrolysis yield on glucan and xylan A process solubilisation yield of 87.8% was calculated for glucan, while a process solubilisation yield of 97.8% was calculated for xylan. A global solubilisation yield of 91.3%, referred to the sum of glucan and xylan present in the raw material is calculated in this process.

The global yield for *Sorghum* is in Table 12

TABLE 12

Enzymatic hydrolysis and process yield of glucan and xylan

|  | *Sorghum* Soak (180° C., 25 min) + Steam 'Explode (200° C., 8 min) |
|---|---|
| Enzymatic hydrolysis yield glucans (%) | 87.9 |
| Enzymatic hydrolysis yield xylans (%) | 98.9 |
| Glucan Process yield (%) | 87.8 |
| Xylan Process yield (%) | 97.8 |
| $FPU/g_{cellulose}$ | 34 |
| $FPU/g_{xylans}$ | 59 |

Tables 13 and 14 show the stream analysis of the feeds as they were taken through the various stages of the process as described in FIG. 1 under the conditions described in the tables using the equipment in this specification.

TABLE 13

SORGHUM

| Material | Control Sorghum | Test1 Sorghum | Test2 Sorghum | Test3 Sorghum | Test4 Sorghum | Test5 Sorghum |
|---|---|---|---|---|---|---|
| Soak (4 from FIG. 1) | | | | | | |
| Time (min) | — | 60 | 100 | 15 | 25 | 25 |
| Temperature (° C.) | — | 160 | 160 | 180 | 180 | 180 |
| Log($R_0$) | — | 3.545 | 3.767 | 3.532 | 3.753 | 3.753 |
| C5 (% wt/wt dry matter basis) | 20.0% | 20.2% | 17.4% | 17.6% | 17.5% | 18.3% |
| C6 (% wt/wt dry matter basis) | 35.2% | 44.9% | 52.0% | 43.3% | 50.6% | 47.5% |
| Furfural (% wt/wt dry matter basis) | 0.000% | 0.007% | 0.005% | 0.033% | 0.058% | 0.021% |
| C5/C6 ratio | 0.570 | 0.450 | 0.335 | 0.407 | 0.346 | 0.385 |
| Furfural/(C5 + C6) * 10^(4) | 0.000 | 1.092 | 0.698 | 5.401 | 8.487 | 3.190 |
| Steam explosion (6 from FIG. 1) | | | | | | |
| Time (min) | | 8 | 12 | 8 | 8 | 8 |
| Temperature (° C.) | | 200 | 200 | 200 | 200 | 200 |
| Log($R_0$) | | 3.847 | 4.024 | 3.847 | 3.847 | 3.847 |
| C5 (% wt/wt dry matter basis) | | 19.9% | 16.7% | 17.4% | 17.2% | 18.3% |
| C6 (% wt/wt dry matter basis) | | 44.8% | 52.0% | 43.3% | 50.6% | 47.5% |
| Furfural (% wt/wt dry matter basis) | | 0.087% | 0.060% | 0.086% | 0.047% | 0.256% |
| C5/C6 ratio | | 0.444 | 0.321 | 0.402 | 0.340 | 0.386 |
| Furfural/(C5 + C6) * 10^(4) | | 13.466 | 8.741 | 14.119 | 6.990 | 38.852 |
| Liquid stream (5 from FIG. 1) | | | | | | |
| C5 (% wt/wt dry matter basis) | | 18.0% | 24.1% | 26.6% | 23.2% | 20.7% |
| C6 (% wt/wt dry matter basis) | | 4.95% | 3.56% | 6.97% | 4.22% | 5.72% |
| Furfural (% wt/wt dry matter basis) | | 0.069% | 0.435% | 0.326% | 0.365% | 0.378% |
| C5/C6 ratio | | 3.638 | 6.749 | 3.825 | 5.501 | 3.623 |
| Furfural/(C5 + C6) * 10^(4) | | 30.091 | 157.376 | 97.113 | 132.866 | 142.787 |
| Global process (20 from FIG. 1) | | | | | | |
| C5 (% wt/wt dry matter basis) | | 19.5% | 19.4% | 19.5% | 19.4% | 19.3% |
| C6 (% wt/wt dry matter basis) | | 35.2% | 35.2% | 35.2% | 35.2% | 35.1% |
| Furfural (% wt/wt dry matter basis) | | 0.083% | 0.190% | 0.140% | 0.153% | 0.292% |
| C5/C6 ratio | | 0.553 | 0.552 | 0.554 | 0.552 | 0.548 |
| Furfural/(C5 + C6) * 10^(4) | | 15.164 | 34.860 | 25.584 | 28.035 | 53.632 |

TABLE 14

ARUNDO

| Material | Control Arundo | Test1 Arundo | Test2 Arundo | Test3 Arundo | Test4 Arundo | Test5 Arundo |
|---|---|---|---|---|---|---|
| Soak (4 from FIG. 1) | | | | | | |
| Time (min) | — | 100 | 100 | 60 | 25 | 15 |
| Temperature (° C.) | — | 160 | 160 | 160 | 180 | 180 |

TABLE 14-continued

ARUNDO

| Material | Control Arundo | Test1 Arundo | Test2 Arundo | Test3 Arundo | Test4 Arundo | Test5 Arundo |
|---|---|---|---|---|---|---|
| $Log(R_0)$ | — | 3.767 | 3.767 | 3.545 | 3.753 | 3.532 |
| C5 (% wt/wt dry matter basis) | 19.3% | 18.4% | 18.4% | 19.0% | 15.5% | 16.1% |
| C6 (% wt/wt dry matter basis) | 37.0% | 47.3% | 47.3% | 45.0% | 51.7% | 49.3% |
| Furfural (% wt/wt dry matter basis) | 0.000% | 0.015% | 0.015% | 0.005% | 0.015% | 0.014% |
| C5/C6 ratio | 0.521 | 0.390 | 0.390 | 0.421 | 0.300 | 0.326 |
| Furfural/(C5 + C6) * 10^(4) | 0.000 | 2.324 | 2.324 | 0.807 | 2.221 | 2.140 |
| | | Steam explosion (6 from FIG. 1) | | | | |
| Time (min) | | 8 | 12 | 8 | 8 | 8 |
| Temperature (° C.) | | 200 | 200 | 200 | 200 | 200 |
| $Log(R_0)$ | | 3.847 | 4.024 | 3.847 | 3.847 | 3.847 |
| C5 (% wt/wt dry matter basis) | | 18.0% | 17.9% | 18.8% | 15.4% | 15.9% |
| C6 (% wt/wt dry matter basis) | | 47.2% | 47.2% | 45.0% | 51.7% | 49.3% |
| Furfural (% wt/wt dry matter basis) | | 0.182% | 0.173% | 0.056% | 0.045% | 0.027% |
| C5/C6 ratio | | 0.380 | 0.379 | 0.417 | 0.298 | 0.323 |
| Furfural/(C5 + C6) * 10^(4) | | 27.980 | 26.625 | 8.855 | 6.751 | 4.145 |
| | | Liquid stream (5 from FIG. 1) | | | | |
| C5 (% wt/wt dry matter basis) | | 20.5% | 20.5% | 18.9% | 26.4% | 26.7% |
| C6 (% wt/wt dry matter basis) | | 2.43% | 2.43% | 3.95% | 3.23% | 4.91% |
| Furfural (% wt/wt dry matter basis) | | 0.120% | 0.120% | 0.067% | 0.174% | 0.248% |
| C5/C6 ratio | | 8.441 | 8.441 | 4.773 | 8.177 | 5.426 |
| Furfural/(C5 + C6) * 10^(4) | | 52.203 | 52.203 | 29.411 | 58.721 | 78.382 |
| | | Global process (20 from FIG. 1) | | | | |
| C5 (% wt/wt dry matter basis) | | 18.5% | 18.5% | 18.8% | 18.7% | 18.9% |
| C6 (% wt/wt dry matter basis) | | 37.0% | 37.0% | 37.0% | 36.9% | 36.9% |
| Furfural (% wt/wt dry matter basis) | | 0.168% | 0.161% | 0.059% | 0.084% | 0.089% |
| C5/C6 ratio | | 0.502 | 0.501 | 0.508 | 0.507 | 0.513 |
| Furfural/(C5 + C6) * 10^(4) | | 30.276 | 29.051 | 10.496 | 15.162 | 15.853 |

The following two series of experiments, 15 and 16 were carried out on a continuous process on wheat straw and arundo respectively. There are some composition with no furfural and this is believed to be caused by an excessive amount of steam keeping the furfural in the vapour stream after steam explosion.

TABLE 15

Wheat Straw

| MATERIAL | Control Wheat Straw | Test1 Wheat Straw | Test2 Wheat Straw | Test3 Wheat Straw | Test4 Wheat Straw | Test5 Wheat Straw |
|---|---|---|---|---|---|---|
| | | Soaking | | | | |
| Temperature (° C.) | — | 155 | 165 | 165 | 165 | 165 |
| Time (min) | — | 97 | 67 | 67 | 67 | 67 |
| $Log(R_0)$ | — | 3.61 | 3.74 | 3.74 | 3.74 | 3.74 |
| | | Steam explosion | | | | |
| Temperature (° C.) | — | 195 | 195 | 200 | 205 | 195 |
| Time (min) | — | 4 | 4 | 4 | 4 | 4 |
| $Log(R_0)$ | — | 3.40 | 3.40 | 3.55 | 3.69 | 3.40 |
| C5 (% wt/wt dry matter basis) | 21.6% | 11.2% | 10.0% | 8.6% | 6.9% | 9.1% |
| C6 (% wt/wt dry matter basis) | 34.9% | 45.3% | 44.2% | 49.2% | 48.9% | 44.9% |
| Furfural (% wt/wt dry matter basis) | 0.00% | 0.00% | 0.00% | 0.00% | 0.00% | 0.00% |
| C5/C6 ratio | 0.62 | 0.25 | 0.23 | 0.18 | 0.14 | 0.20 |
| Furfural/(C5 + C6) * $10^4$ | 0.00 | 0.00 | 0.00 | 0.00 | 0.00 | 0.00 |
| | | Liquid stream | | | | |
| C5 (% wt/wt dry matter basis) | — | 32.9% | 39.6% | 39.6% | 39.6% | 21.5% |
| C6 (% wt/wt dry matter basis) | — | 11.6% | 14.9% | 14.9% | 14.9% | 14.8% |
| Furfural (% wt/wt dry matter basis) | — | 0.90% | 0.83% | 0.83% | 0.83% | 2.95% |
| C5/C6 ratio | — | 2.85 | 2.66 | 2.66 | 2.66 | 1.45 |
| Furfural/(C5 + C6) * $10^4$ | — | 202.42 | 151.76 | 151.76 | 151.76 | 810.50 |
| | | Global process | | | | |
| C5 (% wt/wt dry matter basis) | 21.6% | 14.7% | 14.0% | 13.0% | 11.7% | 10.2% |
| C6 (% wt/wt dry matter basis) | 34.9% | 39.8% | 40.3% | 44.4% | 43.9% | 42.3% |
| Furfural (% wt/wt dry matter basis) | 0.00% | 0.15% | 0.11% | 0.12% | 0.12% | 0.25% |

TABLE 15-continued

| | Wheat Straw | | | | | |
|---|---|---|---|---|---|---|
| C5/C6 ratio | 0.62 | 0.37 | 0.35 | 0.29 | 0.27 | 0.24 |
| Furfural/(C5 + C6) * $10^4$ | 0.00 | 27.07 | 20.49 | 20.18 | 21.70 | 48.02 |

| MATERIAL | Test6 Wheat Straw | Test7 Wheat Straw | Test8 Wheat Straw | Test9 Wheat Straw | Test10 Wheat Straw | Test11 Wheat Straw |
|---|---|---|---|---|---|---|
| *Soaking* | | | | | | |
| Temperature (° C.) | 165 | 165 | 165 | 165 | 165 | 165 |
| Time (min) | 67 | 67 | 51 | 51 | 51 | 37 |
| Log(R0) | 3.74 | 3.74 | 3.62 | 3.62 | 3.62 | 3.48 |
| *Steam explosion* | | | | | | |
| Temperature (° C.) | 200 | 205 | 195 | 200 | 205 | 195 |
| Time (min) | 4 | 4 | 4 | 4 | 4 | 4 |
| Log(R0) | 3.55 | 3.69 | 3.40 | 3.55 | 3.69 | 3.40 |
| C5 (% wt/wt dry matter basis) | 5.8% | 4.9% | 8.5% | 6.0% | 4.7% | 14.5% |
| C6 (% wt/wt dry matter basis) | 44.1% | 44.9% | 44.9% | 43.9% | 40.9% | 49.6% |
| Furfural (% wt/wt dry matter basis) | 0.05% | 0.06% | 0.04% | 0.06% | 0.06% | 0.00% |
| C5/C6 ratio | 0.13 | 0.11 | 0.19 | 0.14 | 0.12 | 0.29 |
| Furfural/(C5 + C6) * $10^4$ | 10.88 | 12.10 | 7.98 | 11.58 | 13.62 | 0.00 |
| *Liquid stream* | | | | | | |
| C5 (% wt/wt dry matter basis) | 21.5% | 21.5% | 19.7% | 19.7% | 19.7% | 26.6% |
| C6 (% wt/wt dry matter basis) | 14.8% | 14.8% | 14.4% | 14.4% | 14.4% | 14.7% |
| Furfural (% wt/wt dry matter basis) | 2.95% | 2.95% | 2.32% | 2.32% | 2.32% | 2.95% |
| C5/C6 ratio | 1.45 | 1.45 | 1.37 | 1.37 | 1.37 | 1.81 |
| Furfural/(C5 + C6) * $10^4$ | 810.50 | 810.50 | 681.43 | 681.43 | 681.43 | 713.38 |
| *Global process* | | | | | | |
| C5 (% wt/wt dry matter basis) | 7.2% | 6.4% | 9.5% | 7.2% | 6.1% | 15.2% |
| C6 (% wt/wt dry matter basis) | 41.6% | 42.4% | 42.1% | 41.2% | 38.5% | 47.6% |
| Furfural (% wt/wt dry matter basis) | 0.30% | 0.31% | 0.25% | 0.26% | 0.27% | 0.17% |
| C5/C6 ratio | 0.17 | 0.15 | 0.23 | 0.18 | 0.16 | 0.32 |
| Furfural/(C5 + C6) * $10^4$ | 61.89 | 63.08 | 48.54 | 54.54 | 60.22 | 27.69 |

| MATERIAL | Test12 Wheat Straw | Test13 Wheat Straw | Test14 Wheat Straw | Test15 Wheat Straw | Test16 Wheat Straw | Test17 Wheat Straw |
|---|---|---|---|---|---|---|
| *Soaking* | | | | | | |
| Temperature (° C.) | 165 | 165 | 165 | 165 | 165 | 170 |
| Time (min) | 37 | 37 | 27 | 27 | 27 | 37 |
| Log($R_0$) | 3.48 | 3.48 | 3.35 | 3.35 | 3.35 | 3.63 |
| *Steam explosion* | | | | | | |
| Temperature (° C.) | 200 | 205 | 195 | 200 | 205 | 195 |
| Time (min) | 4 | 4 | 4 | 4 | 4 | 4 |
| Log($R_0$) | 3.55 | 3.69 | 3.40 | 3.55 | 3.69 | 3.40 |
| C5 (% wt/wt dry matter basis) | 7.6% | 4.9% | 14.0% | 8.0% | 5.7% | 8.2% |
| C6 (% wt/wt dry matter basis) | 50.6% | 47.9% | 49.9% | 49.8% | 48.2% | 53.5% |
| Furfural (% wt/wt dry matter basis) | 0.02% | 0.03% | 0.00% | 0.00% | 0.03% | 0.00% |
| C5/C6 ratio | 0.15 | 0.10 | 0.28 | 0.16 | 0.12 | 0.15 |
| Furfural/(C5 + C6) * $10^4$ | 3.96 | 4.85 | 0.00 | 0.00 | 5.71 | 0.00 |
| *Liquid stream* | | | | | | |
| C5 (% wt/wt dry matter basis) | 26.6% | 26.6% | 29.8% | 29.8% | 29.8% | 27.3% |
| C6 (% wt/wt dry matter basis) | 14.7% | 14.7% | 16.4% | 16.4% | 16.4% | 13.5% |
| Furfural (% wt/wt dry matter basis) | 2.95% | 2.95% | 1.99% | 1.99% | 1.99% | 1.70% |
| C5/C6 ratio | 1.81 | 1.81 | 1.81 | 1.81 | 1.81 | 2.03 |
| Furfural/(C5 + C6) * $10^4$ | 713.38 | 713.38 | 430.07 | 430.07 | 430.07 | 417.42 |
| *Global process* | | | | | | |
| C5 (% wt/wt dry matter basis) | 8.7% | 6.2% | 15.1% | 9.5% | 7.5% | 9.9% |
| C6 (% wt/wt dry matter basis) | 48.5% | 46.0% | 47.6% | 47.4% | 45.8% | 49.9% |
| Furfural (% wt/wt dry matter basis) | 0.20% | 0.20% | 0.14% | 0.14% | 0.18% | 0.15% |
| C5/C6 ratio | 0.18 | 0.13 | 0.32 | 0.20 | 0.16 | 0.20 |
| Furfural/(C5 + C6) * $10^4$ | 34.20 | 37.95 | 21.90 | 25.26 | 33.63 | 25.38 |

TABLE 15-continued

Wheat Straw

| MATERIAL | Test18 Wheat Straw | Test19 Wheat Straw | Test20 Wheat Straw | Test21 Wheat Straw | Test22 Wheat Straw | Test23 Wheat Straw |
|---|---|---|---|---|---|---|
| Soaking | | | | | | |
| Temperature (° C.) | 170 | 170 | 155 | 155 | 155 | 155 |
| Time (min) | 37 | 37 | 72 | 72 | 72 | 72 |
| Log($R_0$) | 3.63 | 3.63 | 3.48 | 3.48 | 3.48 | 3.48 |
| Steam explosion | | | | | | |
| Temperature (° C.) | 200 | 205 | 195 | 200 | 195 | 195 |
| Time (min) | 4 | 4 | 4 | 4 | 4 | 4 |
| Log($R_0$) | 3.55 | 3.69 | 3.40 | 3.55 | 3.40 | 3.40 |
| C5 (% wt/wt dry matter basis) | 5.6% | 4.9% | 14.3% | 10.4% | 18.7% | 17.0% |
| C6 (% wt/wt dry matter basis) | 48.8% | 48.8% | 49.4% | 46.7% | 43.6% | 44.7% |
| Furfural (% wt/wt dry matter basis) | 0.02% | 0.02% | 0.00% | 0.00% | 0.00% | 0.00% |
| C5/C6 ratio | 0.12 | 0.10 | 0.29 | 0.22 | 0.43 | 0.38 |
| Furfural/(C5 + C6) * $10^4$ | 4.46 | 4.39 | 0.00 | 0.00 | 0.00 | 0.00 |
| Liquid stream | | | | | | |
| C5 (% wt/wt dry matter basis) | 27.3% | 27.3% | 22.7% | 22.7% | 29.3% | 31.7% |
| C6 (% wt/wt dry matter basis) | 13.5% | 13.5% | 12.3% | 12.3% | 14.3% | 14.3% |
| Furfural (% wt/wt dry matter basis) | 1.70% | 1.70% | 2.01% | 2.01% | 1.61% | 1.96% |
| C5/C6 ratio | 2.03 | 2.03 | 1.85 | 1.85 | 2.05 | 2.22 |
| Furfural/(C5 + C6) * $10^4$ | 417.42 | 417.42 | 574.97 | 574.97 | 369.56 | 427.34 |
| Global process | | | | | | |
| C5 (% wt/wt dry matter basis) | 7.6% | 6.9% | 15.2% | 11.7% | 19.3% | 18.6% |
| C6 (% wt/wt dry matter basis) | 45.7% | 45.7% | 45.4% | 43.1% | 41.9% | 41.4% |
| Furfural (% wt/wt dry matter basis) | 0.17% | 0.17% | 0.21% | 0.21% | 0.10% | 0.21% |
| C5/C6 ratio | 0.17 | 0.15 | 0.33 | 0.27 | 0.46 | 0.45 |
| Furfural/(C5 + C6) * $10^4$ | 32.67 | 32.95 | 35.37 | 39.14 | 15.65 | 35.64 |

| MATERIAL | Test24 Wheat Straw | Test25 Wheat Straw | Test26 Wheat Straw |
|---|---|---|---|
| Soaking | | | |
| Temperature (° C.) | 155 | 155 | 155 |
| Time (min) | 132 | 132 | 132 |
| Log($R_0$) | 3.74 | 3.74 | 3.74 |
| Steam explosion | | | |
| Temperature (° C.) | 190 | 195 | 200 |
| Time (min) | 4 | 4 | 4 |
| Log($R_0$) | 3.25 | 3.40 | 3.55 |
| C5 (% wt/wt dry matter basis) | 14.0% | 11.2% | 10.8% |
| C6 (% wt/wt dry matter basis) | 45.7% | 45.6% | 45.8% |
| Furfural (% wt/wt dry matter basis) | 0.00% | 0.00% | 0.00% |
| C5/C6 ratio | 0.31 | 0.25 | 0.24 |
| Furfural/(C5 + C6) * $10^4$ | 0.00 | 0.00 | 0.00 |
| Liquid stream | | | |
| C5 (% wt/wt dry matter basis) | 27.8% | 27.8% | 27.8% |
| C6 (% wt/wt dry matter basis) | 12.4% | 12.4% | 12.4% |
| Furfural (% wt/wt dry matter basis) | 2.62% | 2.62% | 2.62% |
| C5/C6 ratio | 2.24 | 2.24 | 2.24 |
| Furfural/(C5 + C6) * $10^4$ | 651.91 | 651.91 | 651.91 |
| Global process | | | |
| C5 (% wt/wt dry matter basis) | 15.6% | 13.1% | 12.7% |
| C6 (% wt/wt dry matter basis) | 42.0% | 41.9% | 42.1% |
| Furfural (% wt/wt dry matter basis) | 0.30% | 0.30% | 0.30% |
| C5/C6 ratio | 0.37 | 0.31 | 0.30 |
| Furfural/(C5 + C6) * $10^4$ | 51.30 | 53.70 | 53.88 |

TABLE 16

| MATERIAL | Control Arundo | Test1 Arundo | Test2 Arundo | Test3 Arundo | Test4 Arundo | Test5 Arundo |
|---|---|---|---|---|---|---|
| *Soaking* | | | | | | |
| Temperature (° C.) | — | 52 | 127 | 127 | 127 | 52 |
| Time (min) | — | 165 | 155 | 155 | 155 | 175 |
| Log($R_0$) | — | 3.630 | 3.723 | 3.723 | 3.723 | 3.924 |
| *Steam explosion* | | | | | | |
| Temperature (° C.) | — | 6 | 6 | 4 | 6 | 6 |
| Time (min) | — | 195 | 200 | 195 | 195 | 195 |
| Log($R_0$) | — | 3.575 | 3.723 | 3.399 | 3.575 | 3.575 |
| C5 (% wt/wt dry matter basis) | 20.0% | 12.1% | 10.4% | 11.0% | 14.0% | 6.8% |
| C6 (% wt/wt dry matter basis) | 33.7% | 42.5% | 49.0% | 53.5% | 45.8% | 51.6% |
| Furfural (% wt/wt dry matter basis) | 0.0% | 0.0% | 0.1% | 0.0% | 0.0% | 0.0% |
| C5/C6 ratio | 0.521 | 0.28 | 0.21 | 0.20 | 0.31 | 0.13 |
| Furfural/(C5 + C6) * $10^4$ | 0.000 | 0.00 | 14.66 | 3.51 | 7.08 | 3.51 |
| *Liquid stream* | | | | | | |
| C5 (% wt/wt dry matter basis) | — | 20.9% | 32.2% | 29.1% | 22.9% | 25.7% |
| C6 (% wt/wt dry matter basis) | — | 12.13% | 18.66% | 16.46% | 20.60% | 11.10% |
| Furfural (% wt/wt dry matter basis) | — | 0.953% | 1.589% | 1.706% | 0.737% | 2.915% |
| C5/C6 ratio | — | 1.720 | 1.724 | 1.769 | 1.113 | 2.314 |
| Furfural/(C5 + C6) * $10^4$ | — | 288.973 | 312.769 | 374.226 | 169.278 | 792.653 |
| *Global process* | | | | | | |
| C5 (% wt/wt dry matter basis) | — | 13.2% | 14.6% | 15.6% | 16.2% | 11.8% |
| C6 (% wt/wt dry matter basis) | — | 38.5% | 43.2% | 44.0% | 39.6% | 40.8% |
| Furfural (% wt/wt dry matter basis) | — | 0.126% | 0.375% | 0.455% | 0.213% | 0.793% |
| C5/C6 ratio | — | 0.344 | 0.338 | 0.355 | 0.409 | 0.290 |
| Furfural/(C5 + C6) * $10^4$ | — | 24.337 | 64.984 | 76.369 | 38.271 | 150.873 |

| MATERIAL | Test6 Arundo | Test7 Arundo | Test8 Arundo | Test9 Arundo | Test10 Arundo | Test11 Arundo |
|---|---|---|---|---|---|---|
| *Soaking* | | | | | | |
| Temperature (° C.) | 52 | 52 | 52 | 52 | 52 | 52 |
| Time (min) | 175 | 175 | 175 | 175 | 175 | 175 |
| Log($R_0$) | 3.924 | 3.924 | 3.924 | 3.924 | 3.924 | 3.924 |
| *Steam explosion* | | | | | | |
| Temperature (° C.) | 2 | 2 | 6 | 2 | 2 | 6 |
| Time (min) | 195 | 210 | 195 | 195 | 205 | 205 |
| Log($R_0$) | 3.098 | 3.540 | 3.575 | 3.098 | 3.393 | 3.870 |
| C5 (% wt/wt dry matter basis) | 6.8% | 4.3% | 5.0% | 6.0% | 5.0% | 4.4% |
| C6 (% wt/wt dry matter basis) | 52.6% | 47.8% | 47.5% | 48.8% | 47.5% | 50.2% |
| Furfural (% wt/wt dry matter basis) | 0.0% | 0.0% | 0.0% | 0.0% | 0.0% | 0.0% |
| C5/C6 ratio | 0.13 | 0.09 | 0.10 | 0.12 | 0.10 | 0.09 |
| Furfural/(C5 + C6) * $10^4$ | 3.60 | 3.82 | 5.08 | 3.26 | 5.08 | 4.34 |
| *Liquid stream* | | | | | | |
| C5 (% wt/wt dry matter basis) | 25.7% | 25.7% | 24.0% | 24.0% | 24.0% | 24.0% |
| C6 (% wt/wt dry matter basis) | 11.10% | 11.10% | 13.08% | 13.08% | 13.08% | 13.08% |
| Furfural (% wt/wt dry matter basis) | 2.915% | 2.915% | 2.328% | 2.328% | 2.328% | 2.328% |
| C5/C6 ratio | 2.314 | 2.314 | 1.835 | 1.835 | 1.835 | 1.835 |
| Furfural/(C5 + C6) * $10^4$ | 792.653 | 792.653 | 627.740 | 627.740 | 627.740 | 627.740 |
| *Global process* | | | | | | |
| C5 (% wt/wt dry matter basis) | 11.7% | 10.8% | 10.6% | 11.3% | 10.6% | 10.5% |
| C6 (% wt/wt dry matter basis) | 41.9% | 36.7% | 37.4% | 38.3% | 37.4% | 38.6% |
| Furfural (% wt/wt dry matter basis) | 0.768% | 0.894% | 0.703% | 0.696% | 0.703% | 0.744% |
| C5/C6 ratio | 0.280 | 0.294 | 0.283 | 0.295 | 0.283 | 0.272 |
| Furfural/(C5 + C6) * $10^4$ | 143.325 | 188.168 | 146.649 | 140.422 | 146.649 | 151.571 |

| MATERIAL | Test12 Arundo | Test13 Arundo | Test14 Arundo | Test15 Arundo | Test16 Arundo | Test17 Arundo |
|---|---|---|---|---|---|---|
| *Soaking* | | | | | | |
| Temperature (° C.) | 127 | 127 | 127 | 97 | 97 | 187 |
| Time (min) | 155 | 155 | 155 | 165 | 165 | 155 |
| Log($R_0$) | 3.723 | 3.723 | 3.723 | 3.901 | 3.901 | 3.891 |
| *Steam explosion* | | | | | | |
| Temperature (° C.) | 6 | 2 | 2 | 6 | 2 | 6 |
| Time (min) | 195 | 195 | 213 | 195 | 195 | 195 |

TABLE 16-continued

Arundo

| | | | | | | |
|---|---|---|---|---|---|---|
| Log($R_0$) | 3.575 | 3.098 | 3.628 | 3.575 | 3.098 | 3.575 |
| C5 (% wt/wt dry matter basis) | 12.3% | 13.2% | 10.1% | 11.4% | 13.6% | 14.1% |
| C6 (% wt/wt dry matter basis) | 42.1% | 36.2% | 48.2% | 45.4% | 46.9% | 45.2% |
| Furfural (% wt/wt dry matter basis) | 0.0% | 0.0% | 0.1% | 0.0% | 0.0% | 0.0% |
| C5/C6 ratio | 0.29 | 0.37 | 0.21 | 0.25 | 0.29 | 0.31 |
| Furfural/(C5 + C6) * $10^4$ | 4.56 | 2.30 | 11.54 | 2.07 | 1.65 | 2.10 |

Liquid stream

| | | | | | | |
|---|---|---|---|---|---|---|
| C5 (% wt/wt dry matter basis) | 24.0% | 24.0% | 24.0% | 24.8% | 24.8% | 26.2% |
| C6 (% wt/wt dry matter basis) | 15.73% | 15.73% | 15.73% | 11.47% | 11.47% | 14.90% |
| Furfural (% wt/wt dry matter basis) | 1.178% | 1.178% | 1.178% | 1.372% | 1.372% | 1.501% |
| C5/C6 ratio | 1.527 | 1.527 | 1.527 | 2.166 | 2.166 | 1.759 |
| Furfural/(C5 + C6) * $10^4$ | 296.352 | 296.352 | 296.352 | 377.872 | 377.872 | 365.159 |

Global process

| | | | | | | |
|---|---|---|---|---|---|---|
| C5 (% wt/wt dry matter basis) | 14.9% | 15.4% | 13.5% | 14.1% | 15.9% | 16.8% |
| C6 (% wt/wt dry matter basis) | 36.2% | 32.2% | 40.2% | 38.6% | 39.7% | 38.4% |
| Furfural (% wt/wt dry matter basis) | 0.283% | 0.244% | 0.341% | 0.284% | 0.287% | 0.344% |
| C5/C6 ratio | 0.413 | 0.479 | 0.336 | 0.364 | 0.400 | 0.438 |
| Furfural/(C5 + C6) * $10^4$ | 55.330 | 51.220 | 63.585 | 53.986 | 51.659 | 62.326 |

| MATERIAL | Test18 Arundo | Test19 Arundo | Test20 Arundo | Test21 Arundo | Test22 Arundo |
|---|---|---|---|---|---|

Soaking

| | | | | | |
|---|---|---|---|---|---|
| Temperature (° C.) | 187 | 67 | 67 | 65 | 65 |
| Time (min) | 155 | 165 | 165 | 165 | 165 |
| Log($R_0$) | 3.891 | 3.740 | 3.740 | 3.727 | 3.727 |

Steam explosion

| | | | | | |
|---|---|---|---|---|---|
| Temperature (° C.) | 2 | 6 | 2 | 4 | 4 |
| Time (min) | 195 | 195 | 195 | 195 | 205 |
| Log($R_0$) | 3.098 | 3.575 | 3.098 | 3.399 | 3.694 |
| C5 (% wt/wt dry matter basis) | 14.8% | 11.4% | 13.1% | 15.91% | 10.80% |
| C6 (% wt/wt dry matter basis) | 43.5% | 44.9% | 46.5% | 44.74% | 49.06% |
| Furfural (% wt/wt dry matter basis) | 0.0% | 0.0% | 0.0% | 0.04% | 0.08% |
| C5/C6 ratio | 0.34 | 0.26 | 0.28 | 0.36 | 0.22 |
| Furfural/(C5 + C6) * $10^4$ | 2.08 | 4.52 | 2.21 | 6.07 | 12.76 |

Liquid stream

| | | | | | |
|---|---|---|---|---|---|
| C5 (% wt/wt dry matter basis) | 26.2% | 20.3% | 20.3% | 24.8% | 24.8% |
| C6 (% wt/wt dry matter basis) | 14.90% | 10.91% | 10.91% | 10.64% | 10.64% |
| Furfural (% wt/wt dry matter basis) | 1.501% | 0.958% | 0.958% | 2.187% | 2.187% |
| C5/C6 ratio | 1.759 | 1.862 | 1.862 | 2.335 | 2.335 |
| Furfural/(C5 + C6) * $10^4$ | 365.159 | 306.865 | 306.865 | 616.267 | 616.267 |

Global process

| | | | | | |
|---|---|---|---|---|---|
| C5 (% wt/wt dry matter basis) | 17.3% | 13.4% | 14.7% | 17.9% | 14.1% |
| C6 (% wt/wt dry matter basis) | 37.4% | 37.1% | 38.3% | 37.2% | 40.0% |
| Furfural (% wt/wt dry matter basis) | 0.331% | 0.238% | 0.232% | 0.511% | 0.576% |
| C5/C6 ratio | 0.462 | 0.362 | 0.385 | 0.480 | 0.353 |
| Furfural/(C5 + C6) * $10^4$ | 60.614 | 47.022 | 43.701 | 92.755 | 106.421 |

Enzymatic Hydrolysis Procedure

This procedure is used to measure the efficacy of a given pretreatment based on a maximum enzyme loading.

This procedure describes the enzymatic saccharification of cellulose and hemicellulose from native or pretreated lignocellulosic biomass to glucose and xylose in order to determine the maximum extent of digestibility possible (a saturating level of a commercially available or in house produced cellulase preparation and hydrolysis times up to one week are used).

Pretreated biomass—Biomass that has been subjected to milling, chemical treatment with water or steam, strong or dilute acid or alkali, or other physical or chemical methods to render the cellulose content of the material more accessible to enzymatic action.

Cellulase enzyme—an enzyme preparation exhibiting all three synergistic cellulolytic activities: endo-1,4-β-D-glucanase, exo-1,4-β-glucosidase, or β-D-glucosidase activities, which are present to different extents in different cellulase preparations.

The pretreated materials were used to enzymatic hydrolysis (EH) in 3-liter fermenter (Infors HT, Labfors 3). EH was run at 7.5% solids concentration, using commercial enzyme solution. The temperature and pH were maintained at 45° C. and 5.0, stirrer was maintained at 400 rpm.

An amount of pretreated material which composition can be summarized in solvent, soluble solid, insoluble solid, is added to a laboratory fermenter. Solvent (water, buffer, antibacterial solution) and catalyst solution are added to this material in order to reach a total solid content of 7.5%. Catalysts solution is calculated to have an activity expressed in FPU/g cellulose of 34.

Catalyst composition is shown in the following table:

TABLE 15

| Enzyme cocktail Name | vol comp % | Density g/ml | specific activity |
|---|---|---|---|
| cellulase complex | 87.4% | 1.08 | 100 FPU/g enzyme solution 1 |
| xylanase | 5.3% | 1.2 | 500 FBG/g enzyme solution 1 |
| hemicellulase | 6.6% | 1.1 | 470 FXU/g enzyme solution 1 |
| enzyme complex | 0.7% | 1.2 | 100 FBG/g enzyme solution 1 |
| Total | 100.0% | 1.09 | | pH is maintained at the desiderate value by the addition of buffer solution or through base or acid solutions.

An aliquot of liquid fraction is taken at different time and analyzed for sugar (glucose, xylose and cellobiose) content. The solid phase at the end of the reaction is recovered. An aliquot of the solid phase is washed three times in 3 time volume of water at 50° C. During washing all the soluble fraction adsorbed on the solid is eliminated. Washed solid is then subjected to moisture and quantitative acid hydrolysis with 72% $H_2SO_4$ following standard methods (NREL) to quantify its composition.

Reagents 7.1 Reagents

Sodium Azide (20 mg/ml in distilled water)

Cellulase enzyme complex of known activity, FPU/mL.

Xylanase enzyme of known of known activity, FXU/mL

Analytical Determination

Raw material was subjected to moisture and extractives determination and to quantitative acid hydrolysis with 72% $H_2SO_4$ following standard methods (NREL/TP-510-42618, NREL/TP-510-42619, NREL/TP-510-42622) The solid residue after hydrolysis was recovered by filtration and considered as Klason lignin. Hydrolyzates were analyzed for monosaccharides (glucose coming from cellulose; xylose and arabinose coming from hemicelluloses) and acetic acid (coming from acetyl groups) by HPLC. Chromatographic determination was performed using a Dionex P680A_LPG equipped with an ion exchange resin Biorad Aminex HPX-87A column under the following conditions: mobile phase, 0.05 mol/L of sulphuric acid; flow rate, 0.6 ml/min; and column temperature, 65° C.

Moisture content of the samples was determined by oven-drying at 105° C. to constant weight.

After pre-treatment, solid residues were recovered by filtration, washed with water, air-dried, and weighted for yield determination. Aliquots of the solid residues from pretreatment were assayed for composition using the same methods as for raw material analysis applied on the washed solid fraction of the stream.

Insoluble solid content of the samples was determined by following standard method (NREL/TP-510-42627).

An aliquot of the liquid phase out of the soaking and the liquid phase accompanying the steam explosion material was oven-dried to a constant weight to determine the content in non-volatile solids (NREL/TP-510-42621)

Liquors were used for direct HPLC determination of monosaccharides, furfural hydroxymethylfurfural and acetic acid. An aliquot of liquors was subjected to quantitative acid hydrolysis with 4% (w/w) $H_2SO_4$ at 121° C. for 60 min, before HPLC analysis (NREL/TP-510-42623). Gluco, arabino, xylo-oligosaccharides concentrations were calculated from the increases in the concentrations of glucose, xylose and arabinose, as analyzed by HPLC, after liquor hydrolysis (NREL method)

NREL Analytical Method

Determination of Structural Carbohydrates and Lignin in Biomass

Laboratory Analytical Procedure (LAP) Issue Date: Apr. 25, 2008

Technical Report NREL/TP-510-42618 Revised April 2008

Determination of Extractives in Biomass

Laboratory Analytical Procedure (LAP) Issue Date: Jul. 17, 2005

Technical Report NREL/TP-510-42619 January 2008

Preparation of Samples for Compositional Analysis

Laboratory Analytical Procedure (LAP) Issue Date: Sep. 28, 2005

Technical Report NREL/TP-510-42620 January 2008

Determination of Total Solids in Biomass and Total Dissolved Solids in Liquid Process Samples Laboratory Analytical Procedure (LAP) Issue Date: Mar. 31, 2008

Technical Report NREL/TP-510-42621 Revised March 2008

Determination of Ash in Biomass

Laboratory Analytical Procedure (LAP) Issue Date: Jul. 17, 2005

Technical Report NREL/TP-510-42622 January 2008

Determination of Sugars, Byproducts, and Degradation Products in Liquid Fraction Process Samples Laboratory Analytical Procedure (LAP) Issue Date: Dec. 8, 2006

Technical Report NREL/TP-510-42623 January 2008

Determination of Insoluble Solids in Pretreated Biomass Material

Laboratory Analytical Procedure (LAP) Issue Date: Mar. 21, 2008

NREL/TP-510-42627 March 2008

We claim:

1. A process for the treatment of ligno-cellulosic biomass comprising the steps of:
    A) soaking a ligno-cellulosic biomass feedstock in a low temperature soaking step in a liquid comprised of water at a temperature in the range of 25 to 100° C. for 1 minute to 24 hours and the low temperature soaking step is followed by a separation step to separate at least a portion of the liquid from the low temperature soaked ligno-cellulosic biomass;
    B) soaking a lingo-cellulosic biomass feedstock in vapor or liquid water or mixture thereof in the temperature range of 145 to 165° C. for a time within the range selected from the group consisting of 1 minute to 24 hours, 1 minute to 6 hours, 1 minute to 4 hours, 1 minute to 3 hours, 1 minute to 2.5 hours, and 1 minute to 2.0 hours to create a soaked biomass containing a dry content and a first liquid;
    C) separating at least a portion of the first liquid from the soaked biomass to create a first liquid stream and a first solid stream; wherein the first solid stream comprises the soaked biomass;
    D) steam exploding the first solid stream to create a steam exploded stream comprising solids and a second liquid;
    E) washing the steam exploded stream with at least a third liquid to create a third liquid stream;
    F) purifying the third liquid stream to create a second purified liquid stream by removing at least a portion of at least one inhibitor selected from the group consisting of acetic acid, formic acid, levulinic acid, furfural, 5-HMF and phenolic compounds; and G) combining the second purified liquid stream with at least a portion of the steam exploded stream.

2. The process according to claim 1, wherein the combination of the second purified liquid stream with at least a portion of the steam exploded stream is done after at least a portion of the steam exploded stream has been hydrolyzed.

3. The process according to claim 1, wherein the process comprises a further step of combining at least a portion of the liquid of the first liquid stream with at least a portion of the steam exploded stream.

4. The process according to claim 3, wherein the combination of the liquid of the first liquid stream with at least a portion of the steam exploded stream is done after at least a portion of the steam exploded stream has been hydrolyzed.

5. A process for the treatment of ligno-cellulosic biomass comprising the steps of:
  A) soaking a ligno-cellulosic biomass feedstock in a low temperature soaking step in a liquid comprised of water at a temperature in the range of 25 to 100° C. for 1 minute to 24 hours and the low temperature soaking step is followed by a separation step to separate at least a portion of the liquid from the low temperature soaked ligno-cellulosic biomass;
  B) soaking a lingo-cellulosic biomass feedstock in vapor or liquid water or mixture thereof in the temperature range of 145 to 165° C. for a time within the range selected from the group consisting of 1 minute to 24 hours, 1 minute to 6 hours, 1 minute to 4 hours, 1 minute to 3 hours, 1 minute to 2.5 hours, and 1 minute to 2.0 hours to create a soaked biomass containing a dry content and a first liquid;
  C) separating at least a portion of the first liquid from the soaked biomass to create a first liquid stream and a first solid stream; wherein the first solid stream comprises the soaked biomass;
  D) steam exploding the first solid stream to create a steam exploded stream comprising solids and a second liquid;
  E) combining at least a portion of the liquid of the first liquid stream with at least a portion of the steam exploded stream; and
  F) purifying the first liquid stream to create a first purified liquid stream by removing at least a portion of at least one inhibitor selected from the group consisting of acetic acid, formic acid, levulinic acid, furfural, 5-HMF and phenolic compounds prior to combining the first liquid stream with at least a portion of the steam exploded stream.

6. The process according to claim 5, wherein the combining with at least a portion of the steam exploded stream is done after at least a portion of the steam exploded stream has been hydrolyzed.

7. The process according to claim 5, wherein the process comprises a further step of combining at least a portion of the liquid of the first liquid stream with at least a portion of the steam exploded stream.

8. The process according to claim 7, wherein the combination of the first liquid stream with at least a portion of the steam exploded stream is done after at least a portion of the steam exploded stream has been hydrolyzed.

9. A process for the treatment of ligno-cellulosic biomass comprising the steps of:
  A) soaking a ligno-cellulosic biomass feedstock in a low temperature soaking step in a liquid comprised of water at a temperature in the range of 25 to 100° C. for 1 minute to 24 hours and the low temperature soaking step is followed by a separation step to separate at least a portion of the liquid from the low temperature soaked ligno-cellulosic biomass;
  B) soaking a lingo-cellulosic biomass feedstock in vapor or liquid water or mixture thereof in the temperature range of 145 to 165° C. for a time within the range selected from the group consisting of 1 minute to 24 hours, 1 minute to 6 hours, 1 minute to 4 hours, 1 minute to 3 hours, 1 minute to 2.5 hours, and 1 minute to 2.0 hours to create a soaked biomass containing a dry content and a first liquid;
  C) separating at least a portion of the first liquid from the soaked biomass to create a first liquid stream and a first solid stream; wherein the first solid stream comprises the soaked biomass;
  D) steam exploding the first solid stream to create a steam exploded stream comprising solids and a second liquid wherein at least some of the second liquid in the steam exploded stream is separated from the steam exploded stream to create a second liquid stream;
  E) combining at least a portion of the liquid of the first liquid stream with at least a portion of the steam exploded stream; and
  F) purifying the first liquid stream to create a first purified liquid stream by removing at least a portion of at least one inhibitor selected from the group consisting of acetic acid, formic acid, levulinic acid, furfural, 5-HMF and phenolic compounds prior to combining the first liquid stream with at least a portion of the steam exploded stream.

10. The process according to claim 9, wherein the combination of the first liquid stream with at least a portion of the steam exploded stream is done after at least a portion of the steam exploded stream has been hydrolyzed.

11. The process according to claim 9, wherein the steam exploded stream is washed with at least a third liquid to create a third liquid stream.

12. The process according to claim 11, wherein the third liquid stream is purified and then combined with at least a portion of the steam exploded stream.

13. The process according to claim 12, wherein the combination of the third liquid stream with at least a portion of the steam exploded stream is done after at least a portion of the steam exploded stream has been hydrolyzed.

* * * * *